United States Patent [19]

Callaghan et al.

[11] Patent Number: 4,969,460
[45] Date of Patent: Nov. 13, 1990

[54] PACEMARKER WITH IMPROVED AUTOMATIC OUTPUT REGULATION

[75] Inventors: Francis J. Callaghan, Miami; William Vollmann, Lauderhill, both of Fla.

[73] Assignee: Telectronics N.V., Curaca, Netherlands Antilles

[21] Appl. No.: 390,527

[22] Filed: Aug. 7, 1989

Related U.S. Application Data

[62] Division of Ser. No. 173,566, Mar. 25, 1988, Pat. No. 4,878,497.

[51] Int. Cl.⁵ ............................................. A61N 1/00
[52] U.S. Cl. ............................. 128/419 PG; 128/697
[58] Field of Search ................. 128/419 PT, 419 PG, 128/419 P, 421, 422, 697

[56] References Cited

U.S. PATENT DOCUMENTS

| | | | |
|---|---|---|---|
| 3,949,758 | 4/1976 | Jirak | 128/419 PG |
| 4,537,201 | 8/1985 | Delle-Vedove et al. | 128/419 PG |
| 4,644,954 | 2/1987 | Wittkampf et al. | 128/419 PG |
| 4,686,988 | 8/1987 | Sholder | 128/419 PT |
| 4,712,555 | 12/1987 | Thornander et al. | 128/419 PG |
| 4,729,376 | 3/1988 | DeCote, Jr. | 128/419 PT |
| 4,759,366 | 7/1988 | Callaghan | 128/419 PG |
| 4,759,367 | 7/1988 | Callaghan | 128/419 PG |
| 4,766,900 | 8/1988 | Callaghan | 128/419 PG |
| 4,766,901 | 8/1988 | Callaghan | 128/419 PG |

FOREIGN PATENT DOCUMENTS

| | | | |
|---|---|---|---|
| 0007189 | 1/1980 | European Pat. Off. | 128/419 PG |
| 0017848 | 10/1980 | European Pat. Off. | 128/419 PG |
| 0129483 | 12/1984 | European Pat. Off. | 128/421 |
| 0232528 | 8/1987 | European Pat. Off. | 128/419 PG |
| 0237767 | 9/1987 | European Pat. Off. | 128/419 PG |

Primary Examiner—Francis Jaworski
Assistant Examiner—George Manuel
Attorney, Agent, or Firm—Gottlieb, Rackman & Reisman

[57] ABSTRACT

A pacemaker which is provided with an improved automatic regulation circuit which is capable of distinguishing between a fusion beat and loss of capture. The failure to sense an evoked potential following a stimulus may be due to either. The cause is determined by generating a high-energy back-up pulse shortly after the stimulus. Failure to capture by the back-up pulse is an indication that there was just a fusion beat; the sensing of an evoked potential is an indication that the stimulus failed to capture.

22 Claims, 23 Drawing Sheets

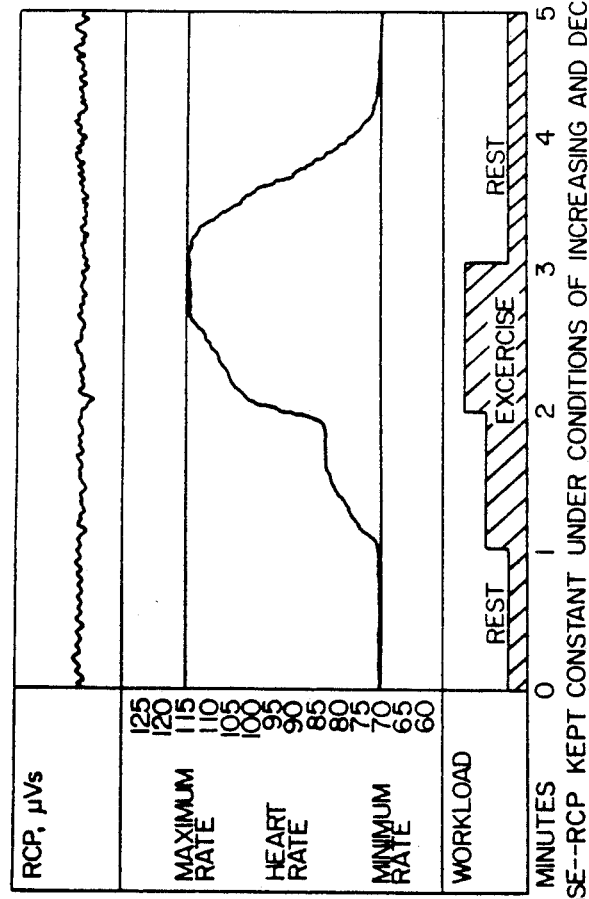
FIG. 10
RATE RESPONSE—RCP KEPT CONSTANT UNDER CONDITIONS OF INCREASING AND DECREASING WORKLOAD BY INCREASING AND DECREASING PACING RATE
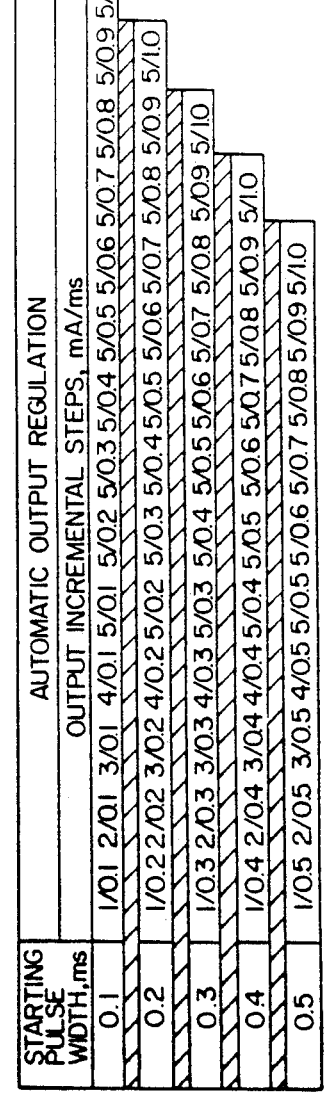
FIG. 11  OUTPUT INCREMENTAL STEPS USED DURING AUTOMATIC OUTPUT REGULATION FUNCTIONS OUTPUT VALUE INCREMENTAL STEPS (o) DURING CAPTURE VERIFICATION WHEN LOSS OF CAPTURE OCCURRED AT 3 mA/0.1 ms (●)

OUTPUT VALUE INCREMENTAL STEPS (o) DURING THRESHOLD SEARCH WITH STARTING PULSE WIDTH AT 0.2 ms (●)

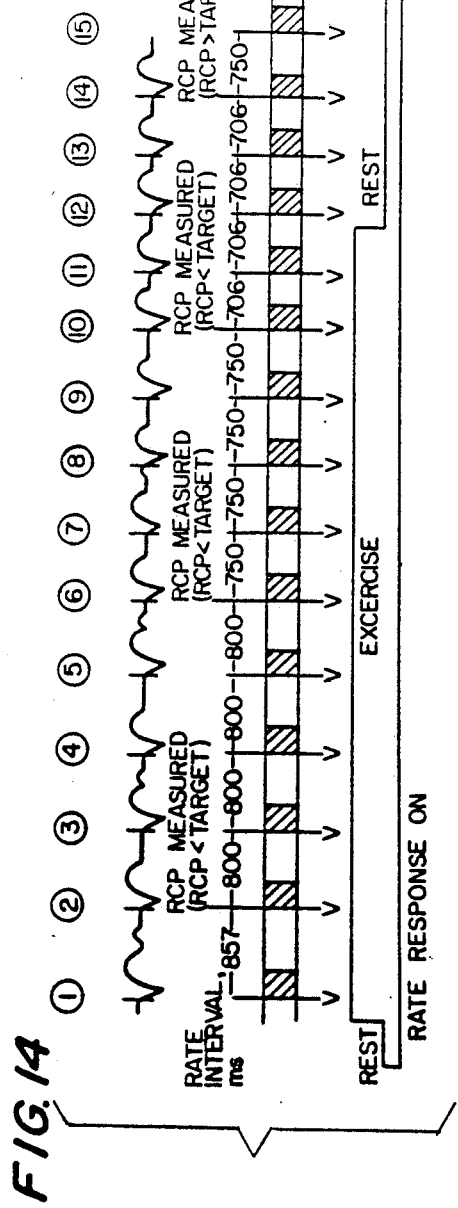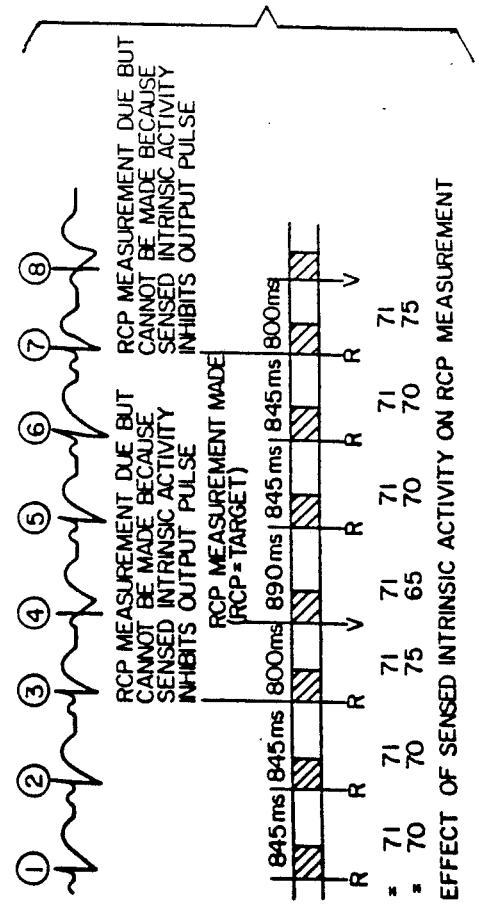
FIG. 14
FIG. 15

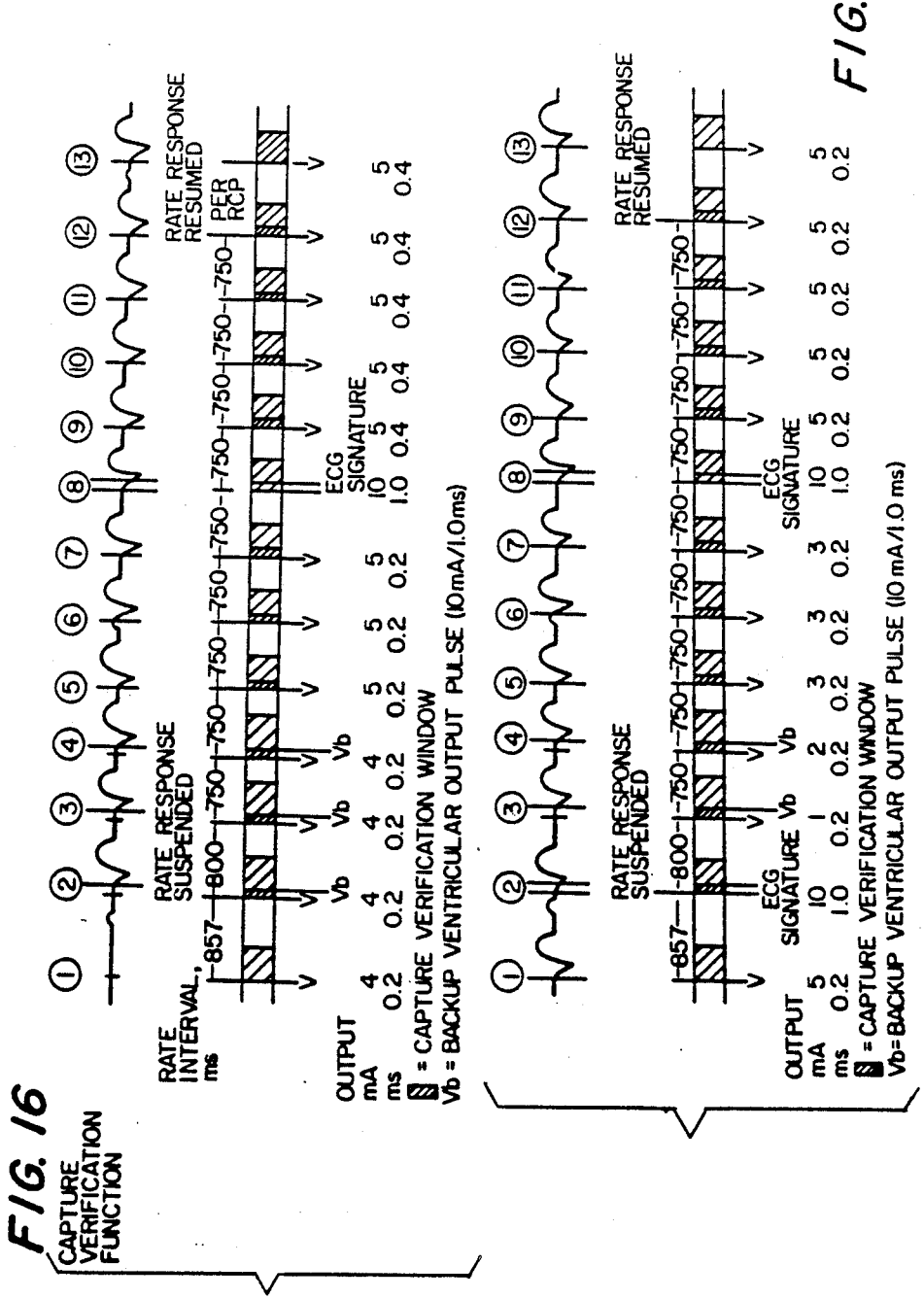

PACEMARKER WITH IMPROVED AUTOMATIC OUTPUT REGULATION

This is a division of application Ser. No. 173,566, filed Mar. 25, 1988 now U.S. Pat. No. 4,878,497.

This invention relates to pacemakers, and more particularly to pacemakers with automatic output regulation.

Automatic output regulation (control of output energy) in a pacemaker, a type of self-adaptation, involves testing for the lowest possible pulse output energy which results in heart capture, a concept not unknown in pacing but one which has not achieved high grades for successful implementation. What often confounds an automatic output regulation circuit is a fusion beat. A fusion beat is a combined intrinsic and paced event; the pacemaker does not have enough time between start of the intrinsic beat and timeout of the escape interval to inhibit generation of a stimulus. A fusion beat is difficult to sense and can lead to an erroneous determination that there has been a loss of capture and that there is therefore a need to increase the output pulse energy.

It is an object of our invention to provide an improved automatic output regulation scheme for an implantable pacemaker, one which is capable of distinguishing between fusion beats and loss of capture.

In the event of an apparent loss of capture, in the illustrative embodiment of the invention, the pacing rate is increased slightly to avoid fusion beats if that is really the problem. Furthermore, a back-up pulse (of high energy) is generated shortly after the failure to sense an evoked response from the preceding ordinary stimulus. If the back-up pulse fails to evoke a response, it is an indication that the preceding stimulus resulted in a fusion beat. Only if the back-up pulse gives rise to an evoked potential is it made clear that the preceding stimulus resulted in a heart capture failure and that the output pulse energy may have to be increased.

Further objects, features and advantages of our invention will become apparent upon consideration of the following detailed description in conjunction with the drawing, in which:

FIG. 10 depicts the manner in which the depolarization gradient (RCP) is maintained constant in a closed-loop control system;

FIG. 11 is a table which shows the way in which output energy is changed during automatic output regulation;

FIGS. 14-17 are timing diagrams which depict several different modes of operation of the pacemaker of our invention;

Figure 27:
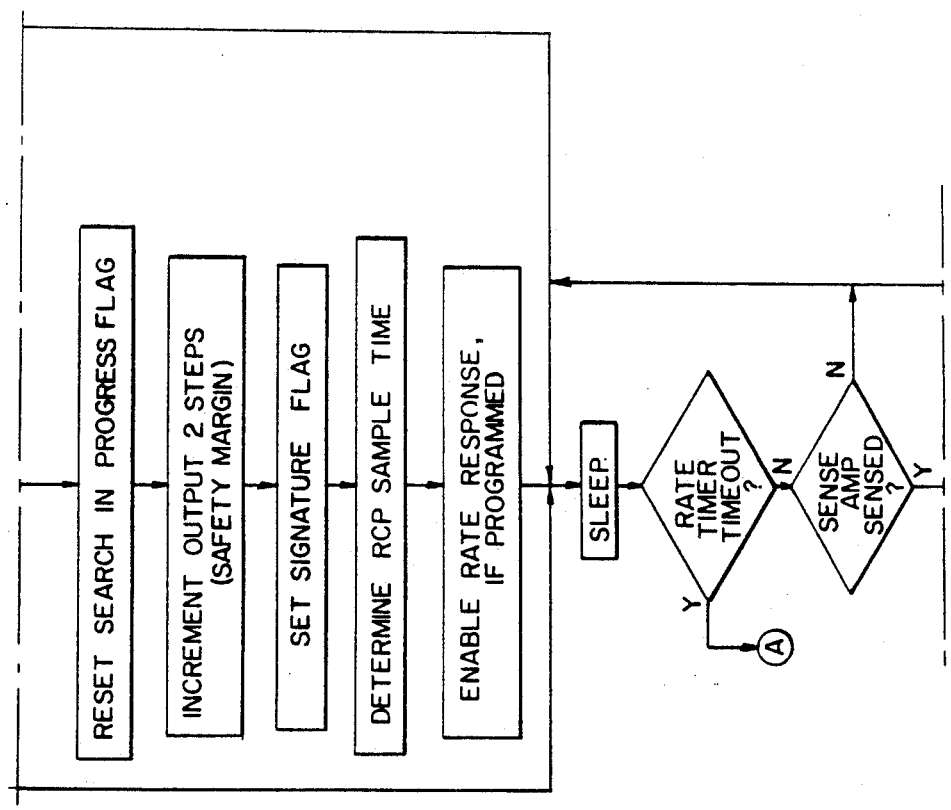
Figure 28:
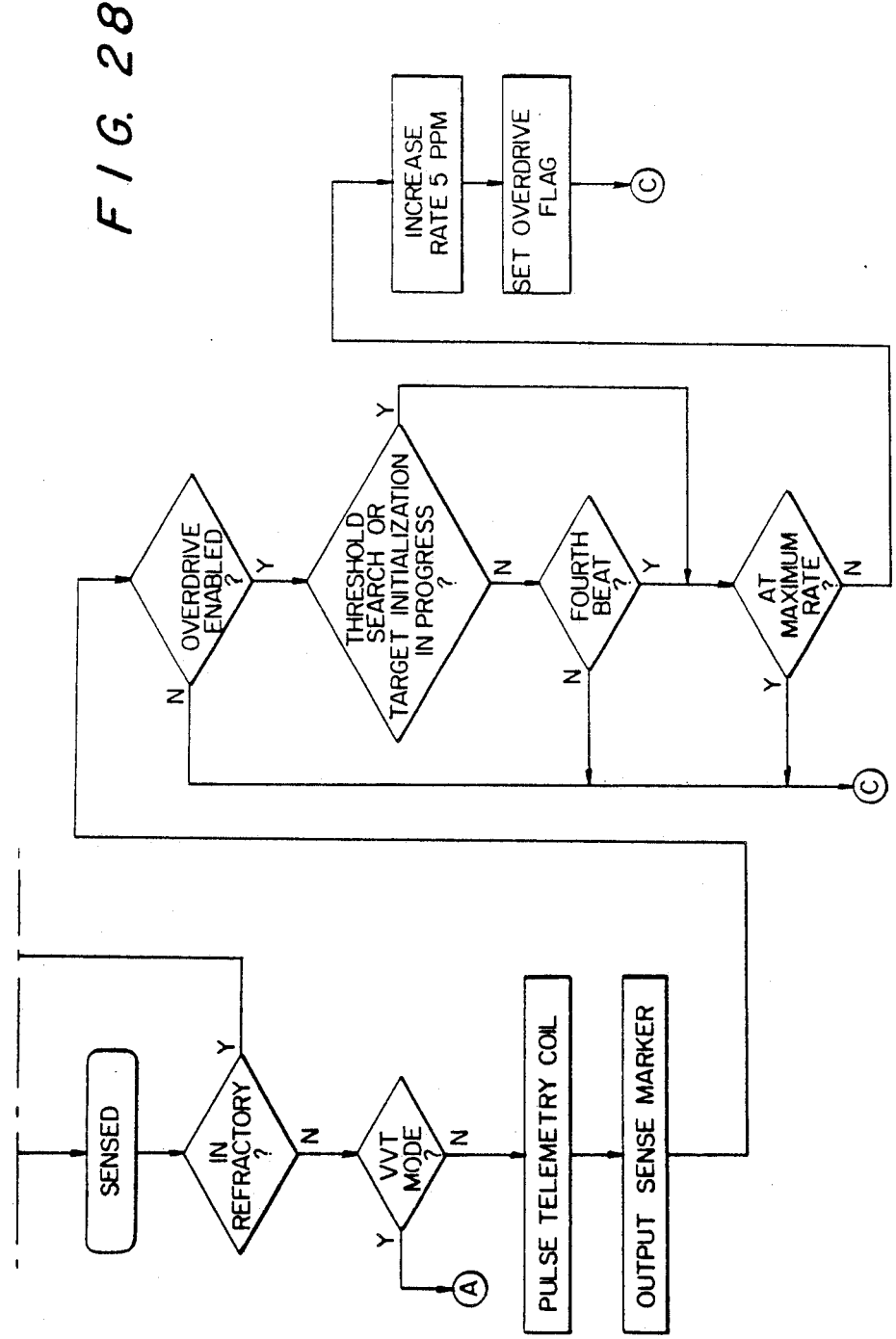
Figure 29:
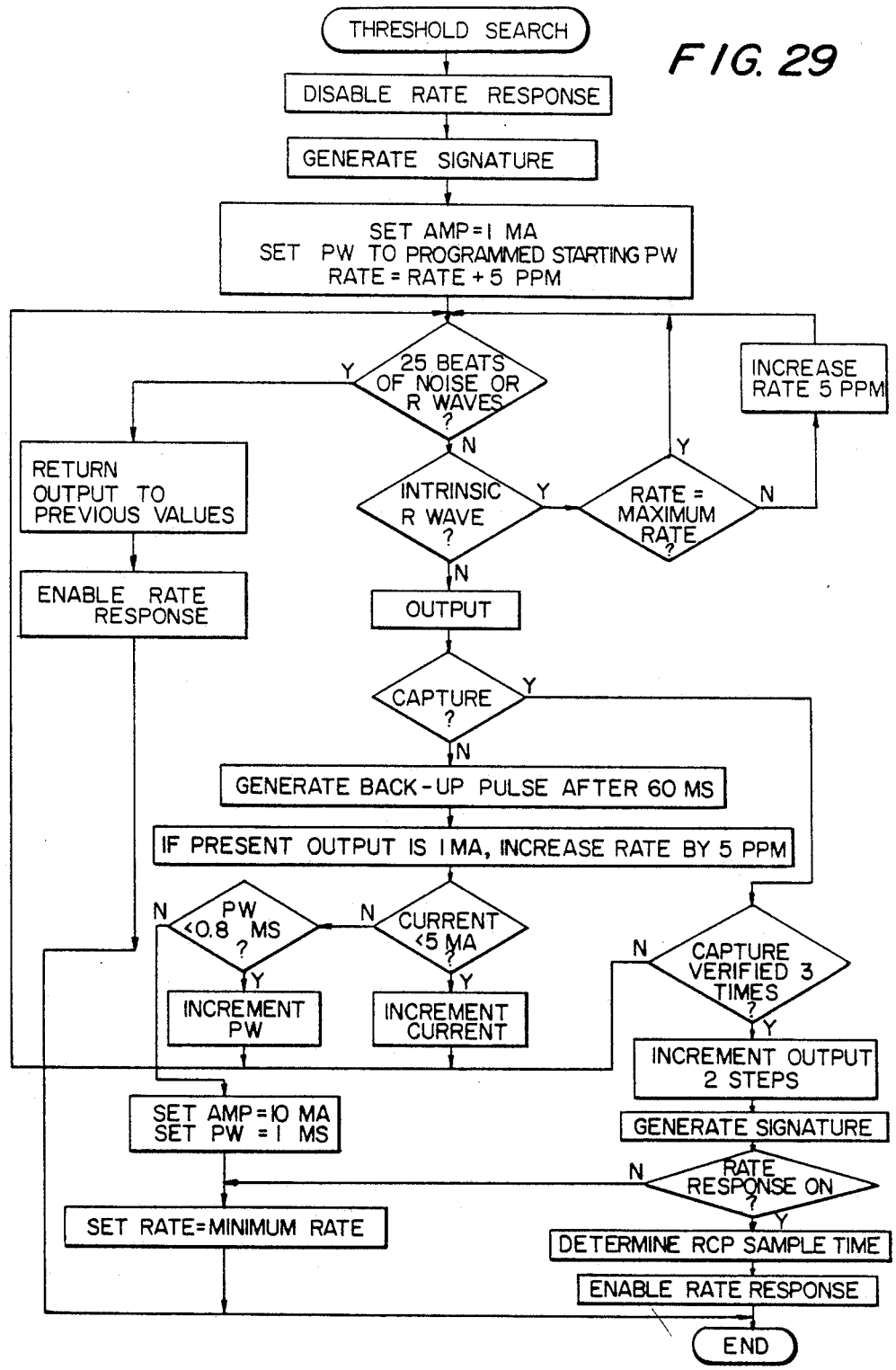
Figure 30:
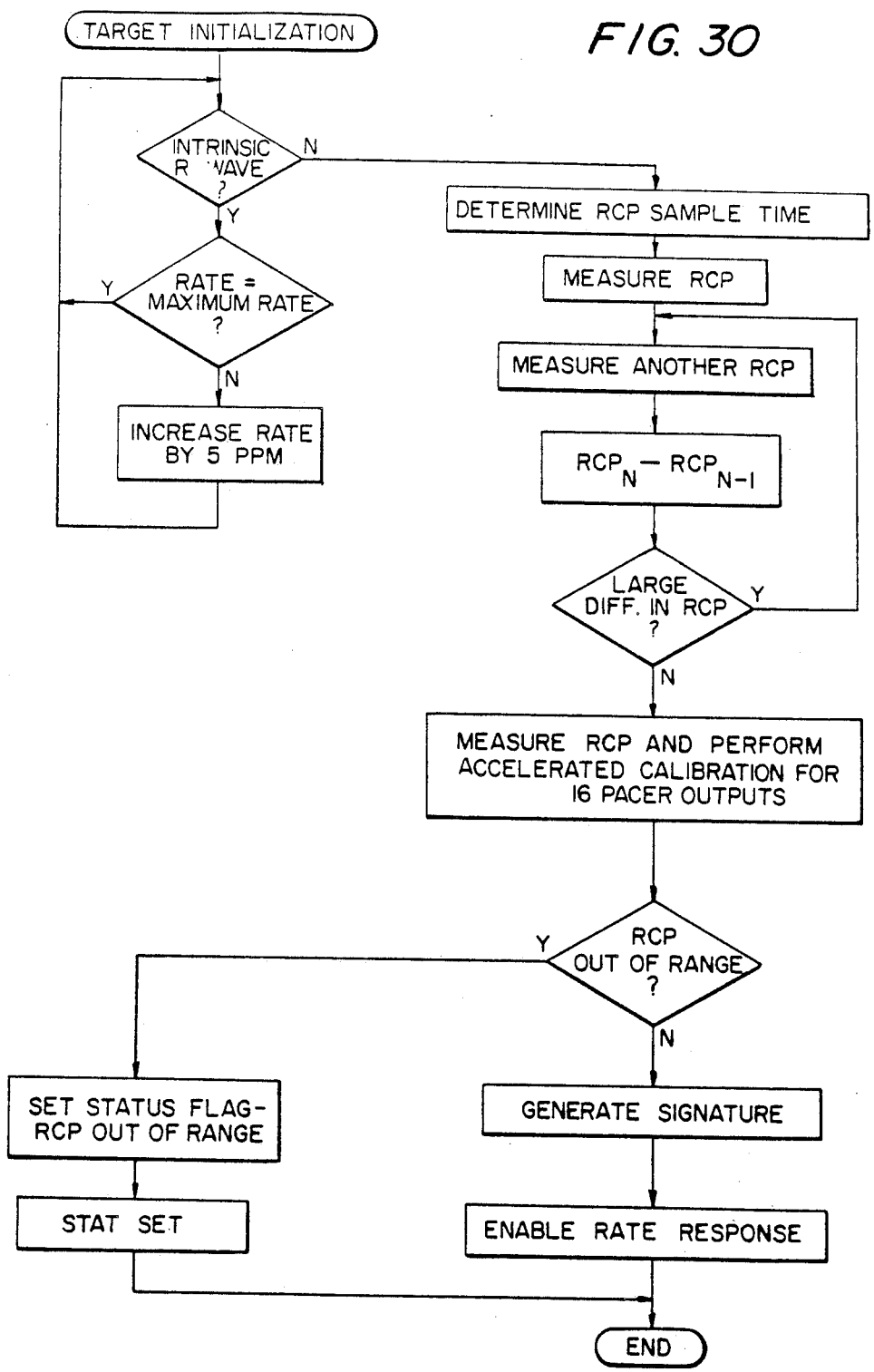

FIGS. 19-28 comprise a low-level flow chart which depicts the methodology of the pacemaker operation; and FIGS. 29 and 30 are high-level flow charts of the threshold search and target initialization procedures.

ILLUSTRATIVE EMBODIMENT—RATE-RESPONSIVE PACEMAKER

In order to describe our automatic output regulation system, some illustrative pacemaker must be chosen as the vehicle for disclosure. We choose a rate-responsive pacemaker, one which has great advantages over those of the prior art.

In order to satisfy the metabolic needs of a patient, it is advantageous to implant a rate-responsive pacemaker. Such a device responds to some rate control parameter (RCP) which is indicative of the body's need for cardiac output. The measured value of the rate control parameter ("MRCP") is used to adjust the pacing rate. In the copending application of Frank Callaghan entitled "Rate Responsive Pacing Using the Magnitude of the Depolarization Gradient of the Ventricular Gradient," Ser. No. 810,877 filed on Dec. 18, 1985, which application is hereby incorporated by reference, there are described numerous rate control parameters which may be used. The particular parameter which is the focus of that application is the depolarization gradient—the integral of the QRS segment of an evoked potential. The magnitude of the depolarization gradient has been found to be an excellent indicator of cardiac output needs.

One of the most formidable problems in designing a rate-responsive pacemaker is to devise an algorithm which relates the MRCP to pacing rate—even assuming that the MRCP is measured correctly. It would be highly advantageous to provide a closed-loop control system for a rate-responsive pacemaker. Such a negative feedback system would allow the control of pacing rate automatically. Instead of having to derive or look up in a table the value of pacing rate which is to be set for each MRCP, a closed-loop control system would simply change the rate in the direction which tends to keep the MRCP constant. If the MRCP tends to change in either direction, the rate adjusts in a direction which returns the MRCP to its value before the change.

What makes the depolarization gradient an excellent rate-control parameter is that increased stress (including both emotional stress and exercise) causes the depolarization gradient to decrease while an increased heart rate causes the depolarization gradient to increase. It is the opposite effects which stress and heart rate have on the depolarization gradient that permits a closed-loop control system to be effected. An increase in stress causes the MRCP to decrease. In the case of increased stress, what is desired is an increased rate. Thus the pacemaker is made to respond to a decrease in MRCP by increasing its rate. But when the rate increases, so does the MRCP; the MRCP increase is in a direction which is opposite to the original MRCP decrease. When the increase in MRCP due to faster pacing cancels the original decrease, the pacing rate stops increasing. The governing rule is that when there is a change in MRCP, the rate is changed so that MRCP moves in the opposite direction, until MRCP is restored. This is a negative feedback system, and it avoids the need for a complex relationship between a measurement value and the way in which the pacing rate should change.

Reference is made to an article entitled "Central Venous Oxygen Saturation for the Control of Automatic Rate-Responsive Pacing," Wirtzfeld et al, PACE, vol. 5, Page 829, November–December 1982. The thesis of this article is that central venous oxygen saturation represents the only rate-control parameter which is suitable for the realization of a closed feedback loop. The thesis is incorrect because the depolarization gradient is another parameter which allows closed-loop control. One of the major advantages which the depolarization gradient has over central venous oxygen saturation is that an additional sensor is not required. The cardiac signal which appears on the pacemaker lead can be processed such that depolarization gradient is determined without requiring the provision of an additional sensor.

Unfortunately, simply selecting a rate-control parameter which theoretically lends itself to closed-loop control is not enough. The object of a closed-loop control system is to maintain a control parameter constant. In the case of a rate-responsive pacemaker, it would appear that it is the MRCP which must remain constant: any change in MRCP caused by stress controls a change in rate which returns the MRCP to the desired (constant) value. (A particular MRCP is suitable, of course, only if maintaining the MRCP constant indeed provides the desired pacing rates for all metabolic needs to be handled.) The problem is that rate control parameters change not only with stress, but also due to other factors. The most important of these is perhaps drugs. Many rate control parameters are affected by the taking of drugs. Thus if an MRCP increases due to the patient having taken a drug, and no change has otherwise taken place in his metabolic needs, it is not desirable for the pacing rate to change in such a way that the MRCP will be returned to its previous value. Furthermore, the operation of a mechanical or chemical sensor may change with time. Even when measuring the depolarization gradient and using it as a rate-control parameter, if for one reason or another the lead shifts in position it is possible for a shift to appear in the MRCP. In such a case, without some way to compensate for a non-stress change in MRCP, a closed-loop control system would effect a permanent shift in pacing rate. The Wirtzfeld et al closed-loop control system did not provide compensation for this type of shift in the rate-control parameter; as far as we know, the Wirtzfeld et al pacemaker has not been commercialized. It is anything but a simple matter to compensate for drifts in a rate-control parameter which are unrelated to stress.

In the illustrative embodiment of our invention, the pacing rate is not changed in a direction which tends to keep MRCP constant. Instead, the pacing rate is adjusted in accordance with a parameter denominated as (MRCP-target), where target is a value indicative of changes in MRCP due to non-stress and non-rate factors (such as changes which result from lead maturation, drugs, etc.). Exactly how the value of target is derived requires careful analysis, although once the concept is grasped it will be seen that there are only three simple rules which must be employed. How target is derived will be described in detail below.

In the illustrative embodiment of the invention, the depolarization gradient is the integral of the QRS waveform of an evoked potential. Not every QRS waveform must be processed, but QRS waveforms must be integrated often enough to allow MRCP up-dating to follow metabolic changes. Since it is evoked potentials which are measured in the illustrative embodiment of the invention, this means that periodically stimulated beats must take place, as opposed to intrinsic beats. Some way must be found to pace the heart periodically even if pacing pulses are not otherwise required. This is accomplished by increasing the pacing rate on an individual beat basis to just above the intrinsic rate when an MRCP sample is required.

Because the heart is paced in the illustrative embodiment of the invention approximately every fourth beat in order that an MRCP sample be taken, it is especially important to use the lowest possible energy in each pulse in order to extend battery life and to minimize distortion of MRCP due to lead polarization. It is therefore particularly important to provide improved automatic output regulation.

Description of Hardware

Figure 1:
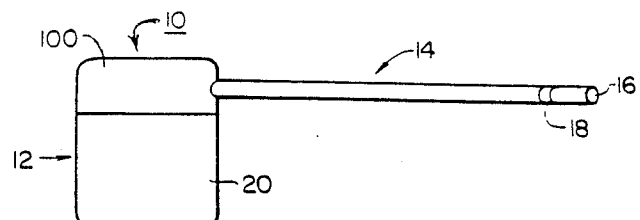
FIG. 1 depicts a pacemaker with a standard bipolar lead.

The single-chamber cardiac pacing system 10 of FIG. 1 includes a pulse generator 12 which is of generally conventional design except as otherwise described herein. Bipolar lead 14 also is of conventional design. For example, tip electrode 16 may be a porous, platinum-iridium, hemispherically-shaped electrode on the distal end of lead 14. Ring electrode 18 is typically spaced at least 0.5 cm from tip electrode 16.

The circuitry of pulse generator 12 is sealed in a hermetic container, for example, titanium can 20, as shown. When the pacer can 20 is treated as an independent electrode, the single-chamber cardiac pacing system 10 carries three electrodes: can 20, tip electrode 16 and ring electrode 18. The operation of the pacing system as described can apply to the ventricular lead of a dual-chamber cardiac pacer. However, for purposes of simplicity of disclosure, the details of operation will be disclosed for only a ventricular pacer.

A pacing cycle begins when an electrical stimulus is emitted from tip electrode 16 to stimulate muscular contraction of at least a portion of the heart. The stimulus is of a magnitude and width which is not harmful to the heart and which is well known to those skilled in the art to evoke a contraction response from the heart muscle. The pulse of electric stimulus 30 is graphed in FIG. 2 as signal A, having a typical duration of 0.1 to 2 milliseconds.

Figure 3:
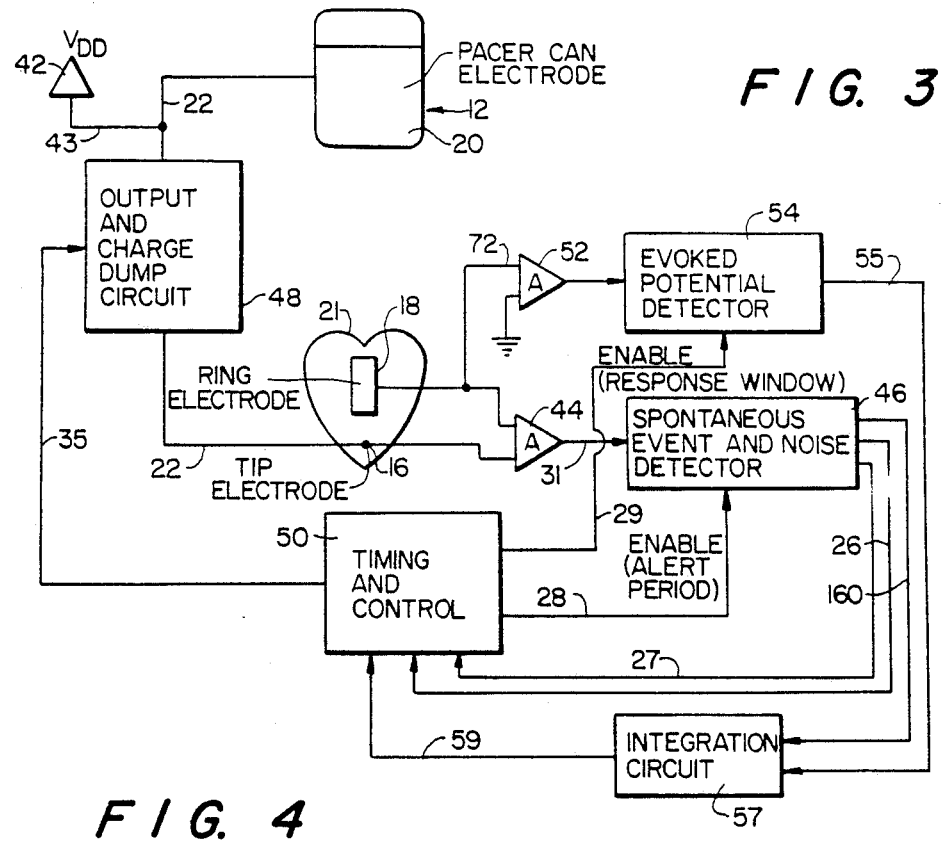
FIG. 3 is a schematic block diagram of a single-chamber pacemaker constructed in accordance with the principles of the present invention.

Referring to the circuit of FIG. 3, pacer can 20 is shown serving as a reference electrode for electrodes 16 and 18. Stimulus 30 is transmitted via conductor 22 to tip electrode 16. The naturally occurring cardiac electrical activity is amplified by sense amplifier 44 and transmitted via line 31 to a spontaneous event and noise detector 46 to begin a timing process. The signal is extended via conductor 26 into timing and control circuitry module 50 which, in turn, has feedback and control lines 28, 29 connected, respectively, to detector 46 and to evoked response detector 54. Likewise, an output from timing and control circuit 50 is connected via line 35 to output and charge dump circuit 48. In the presence of noise, spontaneous event and noise detector 46 extends a corresponding control signal on conductor 27 to the timing and control circuit 50.

Figure 2:
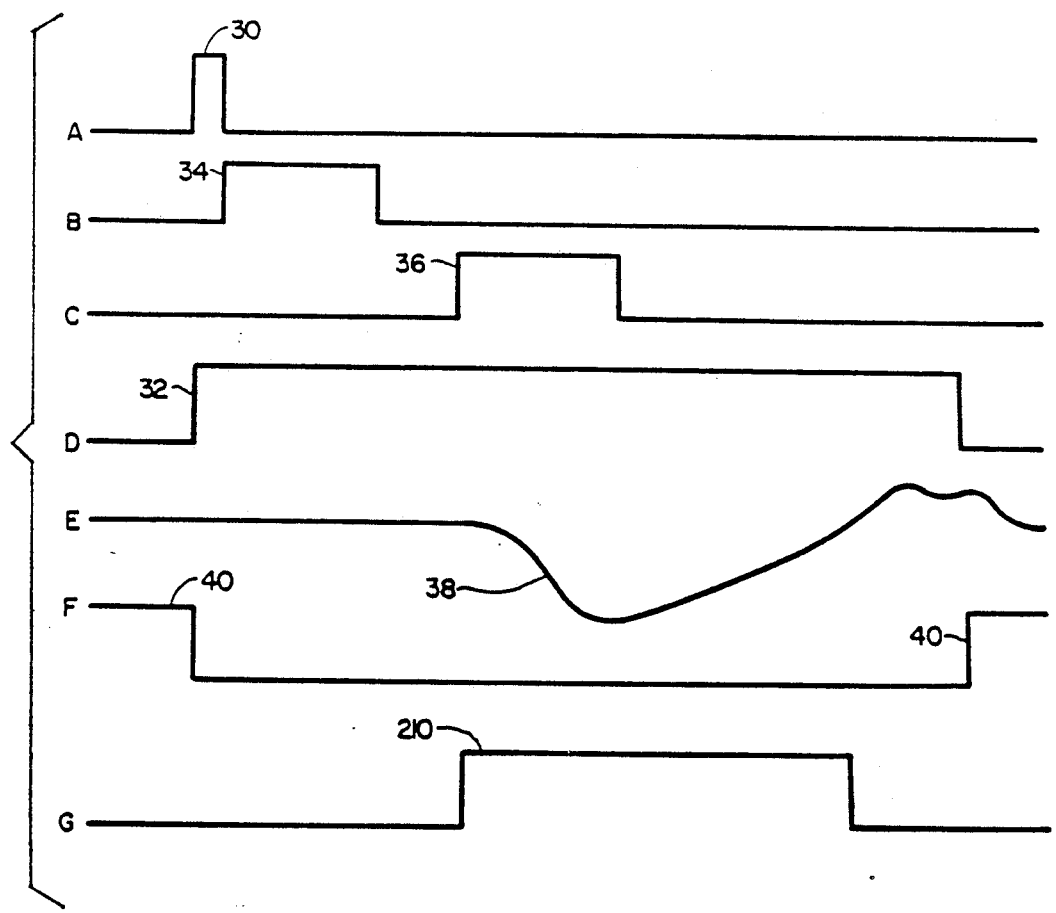
FIG. 2 is a timing diagram which shows the relationships among certain events which take place during a single cardiac cycle.
Figure 4:
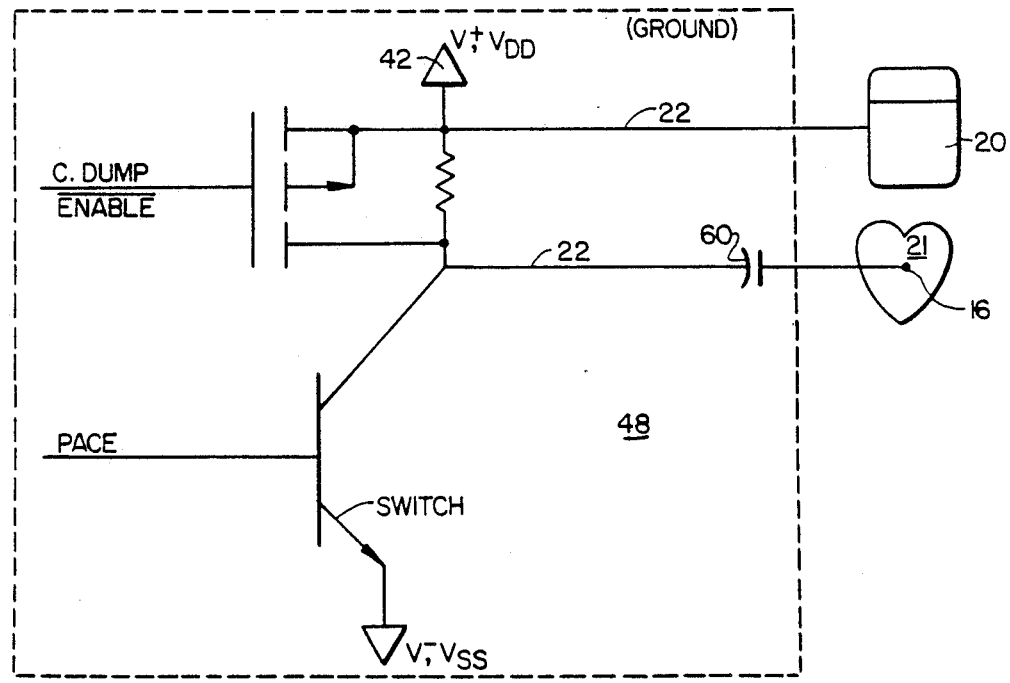
FIG. 4 is a schematic block diagram of the charge dump circuit used in the pacemaker of FIG. 3.

Immediately following the emission of pulse 30 from electrode 16, charge dump circuit 48 is activated, with the charge dump pulse 34 being illustrated as signal B of FIG. 2, the duration of the charge dump being about 5 to 15 milliseconds. The charge dump may be provided using a conventional charge dump circuit 48 such as illustrated in FIG. 4. During the charge dump period, the electrical charge on output coupling capacitor 60 (FIG. 4) and tip electrode 16 are discharged through the heart 21. Thus the post-stimulus polarization potential of electrode 16 is quickly diminished.

Evoked response detector 54 is then activated by timing and control circuit 50 over conductor 29. A window of time 36 is opened as illustrated by signal C of FIG. 2, its magnitude being typically 60 milliseconds. It is only during this time that evoked response detector 54 is activated to detect an evoked electrical response from the heart.

The stimulus from electrode 16 can be seen to be in the unipolar mode. Likewise, detection of the evoked response is unipolar, being detected by ring electrode 18, which communicates over conductor 72 and through amplifier 52 to detector 54. Detector 54 transmits the detected signal via line 55 to integration circuit 57. The integrated signal, which is discussed in detail below, is transmitted to timing and control circuit 50 via line 59.

It is noted that the window of time 36 shown as signal C in FIG. 2 is positioned in a block of time 32 (signal D of FIG. 2) which generally represents a refractory period. However, the evoked response can be detected during a refractory period 32.

Signal E in FIG. 2 shows the evoked cardiac electrical activity 38 within evoked response detection period 36, and which is detected by ring electrode 18. The evoked heartbeat response 38 is detected by ring electrode 18 in the unipolar mode. The detected evoked response is fed via line 55 to integration circuit 57, and the output of the integration circuit is extended via line 59 to timing and control circuit 50.

However, there is a need to detect natural heartbeats to avoid the result of the pacing system disrupting and interfering with the natural heartbeats. To this end, beginning essentially at the end of refractory period 32, during which spontaneous event detector 46 is disabled from sensing cardiac signals, an alert 40 (signal F; FIG. 2) is provided to monitor naturally occurring cardiac electrical activity until such time as the next pulse 30 is applied to tip electrode 16.

Detector circuitry 46 may be activated and shut down by timing and control circuit 50 via line 28. During the alert period 40, both electrodes 16 and 18 operate together in a bipolar configuration, with both electrodes communicating with amplifier 44, which in turn is connected to spontaneous event detector 46. (If desired, intrinsic beats can be sensed using a unipolar configuration.)

In the event of a spontaneous heartbeat, a signal may be sent from spontaneous event detector 46 via line 26 to timing and control circuit 50, to cause the electronics to recycle from any time in the cycle to the beginning of the cycle, without generation of an electric pulse 30 from tip electrode 16. Every time natural cardiac electrical activity takes place during alert period 40, no stimulus will be generated.

In the event, however, that detector 46 does not detect natural cardiac electrical activity during the alert period, timing and control circuit 50 will cause another pulse to be generated via electrode 16.

Figure 5:
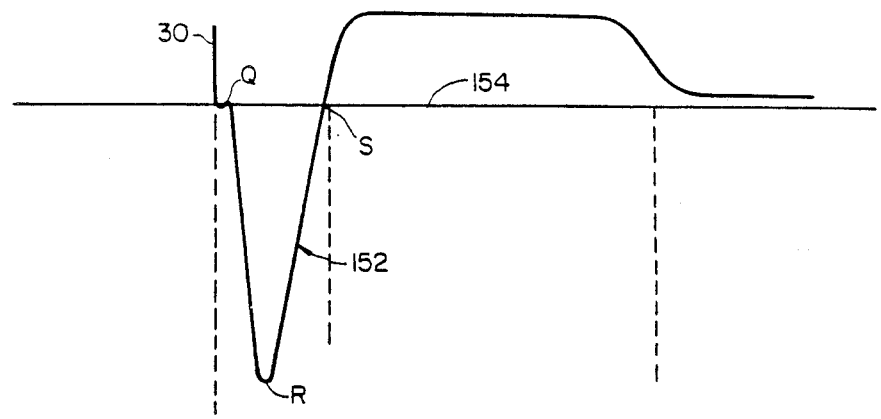
FIG. 5 depicts a sensed evoked potential as a function of time.

Referring to FIG. 5, a typical cardiograph tracing of the changing potential in the ventricle of a heart is shown throughout most of a single cardiac cycle with respect to a reference base line of predetermined voltage, typically zero volts. For purposes of this invention, the Q-point represents the beginning of the R-wave 152 where the voltage trace crosses or is closest to the base line 154, prior to forming R-wave 152. The R-point is the peak of R-wave 152, irrespective of whether the trace is shown in its form of FIG. 5 or in inverted form, which is possible with other recording systems. The S-point is where the trace crosses base line 154.

Figure 6:
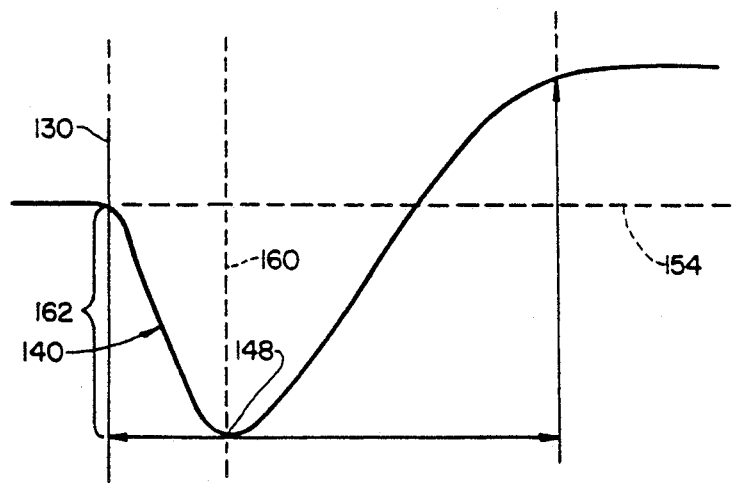
FIG. 6 depicts the depolarization gradient (integrated value) of the evoked potential of FIG. 5.

In operation, as illustrated in FIG. 3, the evoked potential is detected on ring electrode 18. The signal is transmitted via heart amplifier 52 and detector 54 to integration circuit 57 via line 55. The integrated signal 140 is known as the depolarization gradient, and is illustrated in FIG. 6. Referring to FIG. 6, the major parameter of interest to the present invention is the magnitude 162 of the depolarization gradient 140, from the base line 154 to the peak 148.

During periods of heart stress, the area of R-wave 152 decreases in magnitude. Therefore, the depolarization gradient will similarly decrease in magnitude. The depolarization gradient lends itself to detection and analysis. The occurrence of bimodal R waves will not negatively impact upon the value of the depolarization gradient as a stress measuring tool.

The depolarization gradient is calculated and compared to a target value. If the depolarization gradient is equal to the target value, there is no change in the heart pacing stimulus rate. The escape interval remains the same. If the depolarization gradient is smaller than the target value, a determination is made as to whether or not the stimulus rate is at its programmed maximum rate. If it is at its maximum rate, the stimulus rate is not increased. However, if the stimulus rate is less than the programmed maximum rate, the rate is incremented by some predetermined value. Should the depolarization gradient increase, indicating a reduction in stress, the determination is made as to whether or not the rate of stimulation is at its minimum programmed rate. If it is at the programmed minimum rate, there is no further decrease in rate. If it is not at its minimum programmed rate, the rate of the stimulation is decreased by some predetermined value.

Spontaneous electrical events such as those conducted from the atrium to the ventricle via the cardiac conduction pathway of those arising within the ventricle itself (premature ventricular contractions) are detected. These signals are amplified by the amplifier 44 and detected in the spontaneous event and noise detector 46. The timing and control circuit 50 acts upon these events to reset the escape interval. (Further, these spontaneous electrical events may be integrated if desired, and the depolarization gradient may be determined. Rate changes or escape interval changes may be implemented based on the depolarization gradient of the spontaneous electrical events in the same manner that they are implemented based on the depolarization gradient of the evoked potentials. To this end, the integration circuit 57 of FIG. 3 is shown as receiving the signal from spontaneous event and noise detector 46 via line 160, although only evoked potentials are processed in the illustrative embodiment of the invention.)

Figure 7:
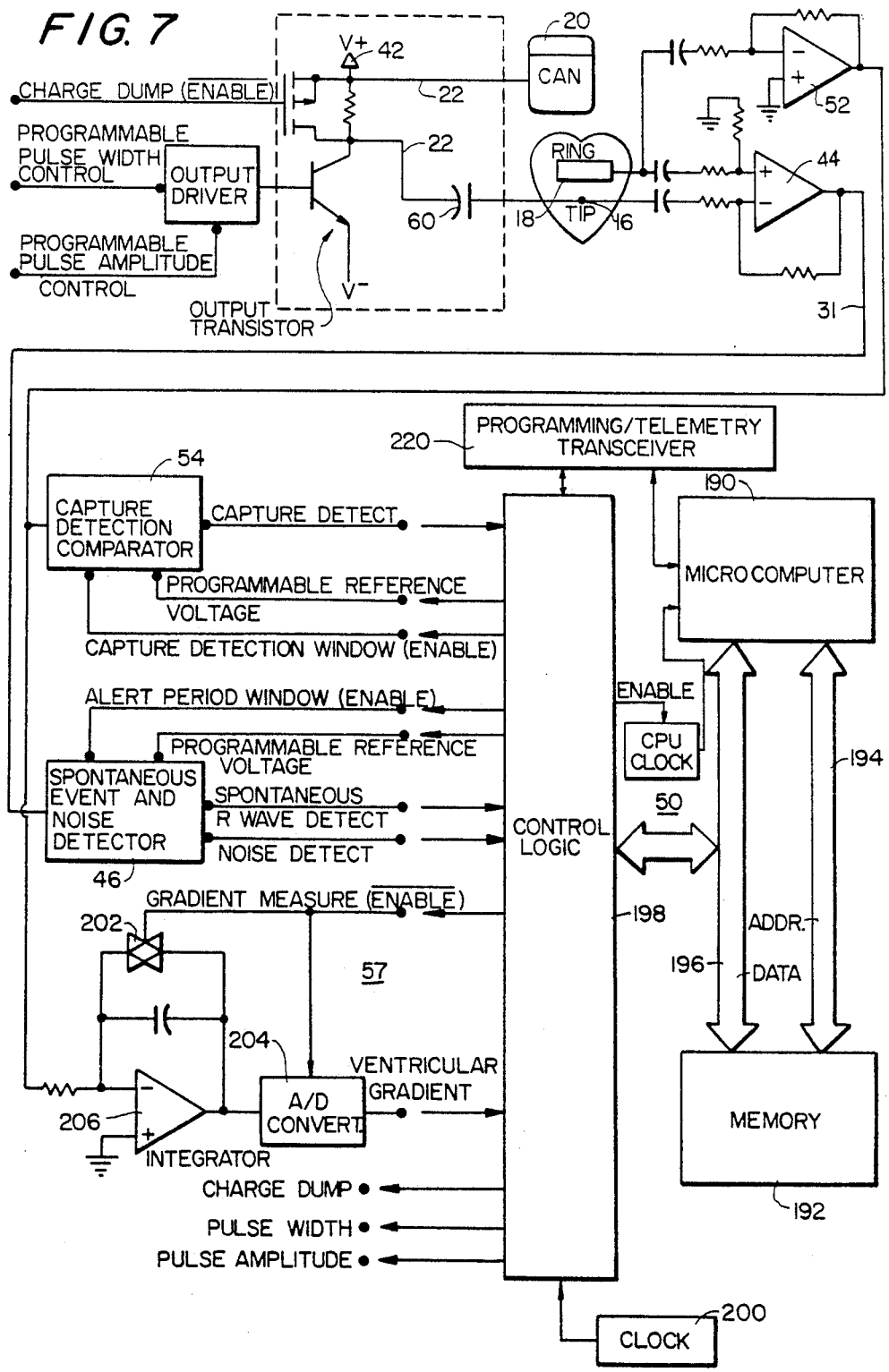
FIG. 7 is a more complete representation of the illustrative embodiment of the invention.

A relatively detailed schematic diagram of the pacer electronics is presented as FIG. 7. Referring to FIG. 7, it is seen that the same reference numerals are used for the same components of FIG. 3. Timing and control circuit 50 comprises a microcomputer 190 which addresses a memory 192 via address bus 194. Data bus 196 is coupled between microcomputer 190 and memory 192, and conventional control logic 198 is coupled to data bus 196. A crystal controlled clock 200 is used for providing appropriate clock pulses for the system. The functions of the control logic inputs and outputs are designated. The drawing of FIG. 7 also shows a programming/telemetry transceiver 220 for allowing supervisory information and data to be telemetered out for reception by a programmer or other receiving device, and for allowing the pacemaker to be programmed by an external programmer, as is well known in the art.

Control logic circuit 198 provides a gradient measure enable signal to electronic switch 202 and to analog-to-digital converter 204 which is at the output of an integrating amplifier 206. It can be seen that the amplified potential sensed at ring 18 is applied to the negative input of the integrating amplifier 206 which, when enabled, provides an amplified analog output that is converted to digital data by means of analog-to-digital converter 204. The digital data contains the depolarization gradient information, which is provided to the control logic circuit 198 whereby appropriate timing of the stimulation pulses is achieved in response thereto.

The gradient measure enable signal 210 is illustrated as signal G on FIG. 2. It commences at the same time that the capture detection window 36 commences and the gradient measure enable signal 210 continues for up to 130 milliseconds. The several control signals depicted on FIG. 7 are for the most part self-explanatory. For example, it will be apparent that spontaneous event and noise detector 46 is provided with a programmable reference voltage which serves as a threshold. It is enabled to sense R waves by an alert period window signal. The two signals which it provides to the control logic represent the sensing of an intrinsic beat or the presence of noise.

The Depolarization Gradient As A Rate-Control Parameter

Figure 8:
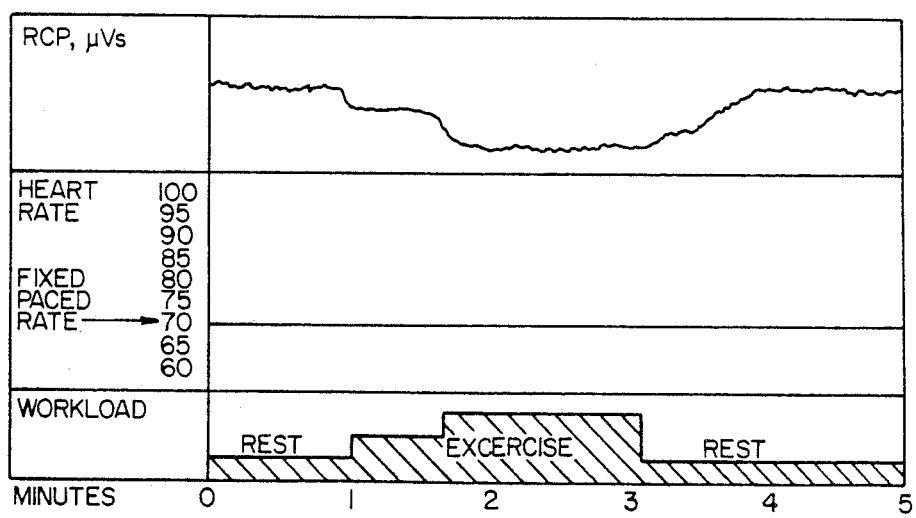
FIG. 8 depicts the manner in which the depolarization gradient (RCP) changes with stress.
Figure 9:
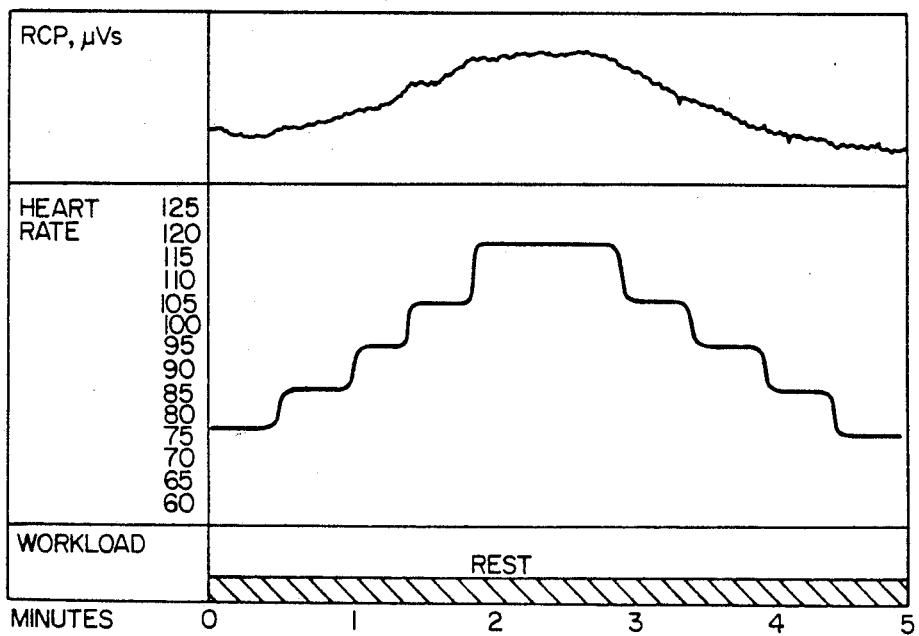
FIG. 9 depicts the manner in which the depolarization gradient (RCP) changes with pacing rate.

The reason that the depolarization gradient lends itself to closed-loop control is exemplified by FIGS. 8, 9 and 10. The key to the closed-loop control is that the physiological effects of emotional or physical stress cause the RCP to become smaller, whereas increased heart rate causes the RCP to become larger.

The opposite effects of stress and heart rate on the depolarization gradient are shown in FIGS. 8 and 9, in which the RCP refers to the depolarization gradient. The bottom of the first graph shows the patient at rest, then starting to exercise, then exercising more strenuously, and finally returning to rest. This is referred to as the workload. The patient's heart is paced at a fixed rate in the case illustrated in FIG. 8, at a rate of 70 pulses per minute. The top of the graph shows the RCP, measured in microvolt-seconds, as decreasing with increasing stress. Thus FIG. 8 shows how the RCP decreases if the heart rate does not increase when the patient is under stress. In contrast, the graph of FIG. 9 shows what happens if the heart rate is increased to a value higher than that required for the current state of stress; in such a case the RCP increases. As seen in FIG. 9, the patient is at rest but the heart rate is arbitrarily increased and then decreased over a period of 5 minutes. The RCP is seen to increase with increasing rate. Together FIGS. 8 and 9 show that increased stress and increased heart rate have opposite effects on the RCP.

It is this phenomenon that allows a stabilizing feedback mechanism to be established. The graph of FIG. 10 depicts the rate response of the closed-loop control mechanism of our invention. As stress increases (an increase in exercise), the RCP tends to decrease (FIG. 8); however, any tendency for the RCP to decrease causes the control mechanism to increase the heart rate. The increase in heart rate restores the RCP to its pre-change value (FIG. 9). The net result of maintaining the value of RCP constant is that the heart rate follows the patient's workload. This is the significance of what is shown in FIG. 10: simply by maintaining the RCP constant, the heart rate can be made to follow the metabolic needs of the patient without any complicated relationship between RCP and heart rate having to be devised.

The Rate-Response Algorithm

The basic rule is that when there is a change in the measured value of the RCP (MRCP), the rate should be increased or decreased in the direction which restores MRCP. But while the basic rule is simple to state, it is not sufficient to implement a closed-loop control system. The reason is due to changes which occur over long periods of time (long compared to how fast MRCP changes due to stress) because of other factors, e.g., drugs. If a drug causes MRCP to decrease and to remain lower than it otherwise would be, then the pacer will cause the pacing rate to be higher than it should be; the pacer does not know why MRCP decreased and would blindly follow the rule to increase the rate so that MRCP remains constant. Simple control of the type described does not work in the absence of compensation for changes in MRCP due to factors other than those related to stress.

The solution is to control rate in a feedback network not so that MRCP stays constant, but so that (MRCP-target) stays constant. Target is a value which ideally changes with non-stress "inputs"; it changes the same way as those "inputs" affect MRCP. Drugs may change MRCP, but if they also change target by the same amount, the control parameter—(MRCP-target)—affects rate in accordance with only changes in MRCP due to stress. The operative rule is to change rate in a direction which compensates for changes in (MRCP-target), with target remaining constant over the short term and thus allowing the pacer to respond to stress changes.

Now if (MRCP-target) decreases, for example, it is assumed that it is decreasing because MRCP decreased in response to the patient starting to exercise. The MRCP still changes in accordance with stress and rate in opposite directions (which is why the control system works in the first place). The MRCP also still changes in accordance with other "inputs", but now the effect of these other inputs on the control loop is cancelled by having target respond to these inputs in the same way that MRCP does, and by using (MRCP-target) as the control parameter. The control system is not only closed-loop, but adaptive as well.

The question is how to get target to reflect changes in MRCP which are due to non-stress factors, i.e., how to get the pacer to self-adapt. We will give some rules to follow, and then see why they work.

What is desired is that the pacer pace at or near the minimum rate in the absence of exercise, i.e., most of the time the minimum rate is wanted. Whenever the rate is above the minimum rate (due to rate respose taking place), the pacer imposes a very small bias which slowly returns the rate to the minimum by decreasing target; this is done just in case the reduced MRCP which is causing pacing above the minimum rate is really due to drift. The bias is so small that the tendency to decrease the rate is overpowered by changes in the rate-response system due to stress (increased or decreased rate). Eventually a return is made to minimum rate. The usual reason is that the patient has stopped exercising. But if there was a drift and the rate could not be returned all the way by the control system, a full return will still occur because of the slowly decreasing target value. As (MRCP-target) thus slowly increases, the rate slowly decreases as desired, all the way down to minimum rate. Thus Rule 1, applicable during rate-responsive pacing, is to decrease target slightly during each MRCP measurement cycle, if the present rate is above the minimum rate. Changing target this way is in addition to changing the rate in accordance with the new value of (MRCP-target).

Consider now a positive value of (MRCP-target) when minimum rate is reached. Pacing is at the minimum rate and is not going any lower. MRCP may have changed due to drift, but the present MRCP is what is now being measured for minimum rate. No more changes in rate are desired (in the absence of stress changes); the rate is where it should be. At the minimum rate, (MRCP-target) should equal zero. The reason is that should stress increase, i.e., the patient start to exercise, it is desired that (MRCP-target) go negative so it can control a rate increase. If target is too small and (MRCP-target) is positive, (MRCP-target) may not go negative when MRCP decreases. Before it could become negative and control a rate increase, MRCP would have to decrease appreciably just to get rid of the unnecessary positive residue (introduced by forcing target down during rate-response pacing, and possibly drift). To avoid this kind of lag, when pacing is at the minimum rate (MRCP-target) is made equal to zero by increasing target as much as necessary—until it equals MRCP. When exercise then starts, the slightest decrease in MRCP due to stress will make (MRCP-target) negative, and the rate will start increasing. So Rule 2 is to increase target until it equals MRCP whenever minimum rate is achieved. Moreover, target is increased very rapidly so that the pacemaker will be ready to increase the pacing rate as soon as exercise commences.

When minimum rate is achieved, (MRCP-target) cannot be negative. A negative value for (MRCP-target) causes the rate-response system to control a rate increase, i.e., above minimum rate; thus (MRCP-target) cannot be negative at minimum rate. If (MRCP-target) is zero at minimum rate, there is nothing to do; there is equality between MRCP and target, rate response leaves the rate as is, and it is just where it is desired. In fact, when (MRCP-target) is positive, target is increased precisely so that a difference of zero is obtained. When the pacing rate is above minimum rate due to rate response, on the other hand, target is reduced continuously, albeit slowly. As target is decreased, so is rate. What happens is that eventually (MRCP-target) is positive when minimum rate is obtained—either because target has been decreased by the built-in bias, or, more commonly, the patient has stopped exercising. It is at this time that target is rapidly increased until it equals MRCP.

The original question was how to derive a value for target which reflects changes in MRCP which are due to non-stress factors. The question has been answered by the two rules just given. The pacer may not know what the non-stress factors have done to MRCP. But it does know that the feedback loop, controlled by (MRCP-target), is controlling pacing at the minimum rate. The pacer may be measuring a different value of MRCP than it did yesterday for the same conditions, but whatever the new value, target is just right for it to give the minimum rate for this particular value of MRCP. And once the correct value of target is had for one rate, it can be used for all rates; target stays constant over the short term. When minimum rate is reached, target may be too small [(MRCP-target) is positive] and must be increased because the built-in bias made it too small by continuously reducing it while rate response was operative. Whenever a return is made to minimum rate, as always happens, the pacer adjusts a target to correct for what it did to it and also for non-stress inputs which have occurred since the last time a departure was made from minimum rate.

How fast target must be decreased (whenever the current rate is above minimum) depends on the patient. If he will exercise for long periods of time, then since target is continuously decreased the pacing rate may eventually return to minimum rate even though he is still exercising. So for such a patient, target should be decreased very slowly. For the patient who takes drugs every two hours and whose MRCP keeps changing rapidly (due to things other than stress), calibration should be much faster. An advantage of the design is built-in safety. No one, not even an exercising patient, should be paced at high rates forever. Even his slow calibration speed eventually causes target to decrease enough to lower the rate. But the slow calibration speed lets him exercise for lengthy periods of time before the automatic reducing of target eventually has much of an effect on reducing the rate. As will be described, three calibration speeds during rate-response pacing can be programmed.

Suppose a patient exercises for a long time, until target has been reduced appreciably. When he stops, MRCP increases. Now (MRCP-target) is much greater than it otherwise would be because target was reduced as a result of the built-in bias (Rule 1, applicable during rate response). The rate now drops down, usually all the way to the limit of the minimum rate. If the patient starts exercising again, (MRCP-target) would still be high due to the low value of target, and rate response would keep rate low even though a higher rate is wanted. That is why, at minimum rate, target is increased very rapidly. In just a few minutes, target rises to MRCP. When exercise then resumes and MRCP drops, target is high enough to allow a high rate to be controlled. Calibration is orders of magnitude faster when target is being increased at minimum rate than it is when the rate is above minimum rate and target is being decreased. (Actual calibration speeds will be discussed below.)

The decrease in target during rate-response pacing is designed to force a return to minimum rate at which time target can be corrected. Usually, minimum rate will be achieved because the patient stops exercising at which time target is corrected to compensate for non-stress effects on MRCP. Decreasing target during rate-response pacing to force a return to minimum rate is the pacer's fail-safe mechanism.

Thus far two cases have been considered: (1) pacing above minimum rate [target is decreased at one of three calibration speeds], and (2) pacing at minimum rate [only if (MRCP-target) is positive is target increased, very rapidly]. But there is a third case—an intrinsic rhythm faster than the minimum rate. As will be described below, on every fourth beat overdriving (pacing at a rate faster than the intrinsic rate) is commenced until an evoked response is obtained so that MRCP can be measured. The question is what is done to target in this third case.

An intrinsic rhythm is really a minimum rate; it is higher than the programmed value, but the intrinsic rate will not permit the pacer to pace more slowly. So it is treated like case 2, with one difference: target is increased as in case 2, but at the programmed calibration speed used for case 1 (not the very fast speed of case 2). This is Rule 3. The reason is that the intrinsic rate may be due to some pathological factor. When target is increased, in effect the pacer is controlled to pace at a higher rate. If target is rapidly increased, as in case 2, all rates would be biased upward just because momentarily there was a pathologically high intrinsic rate. To avoid this, target is increased slowly when the intrinsic rate is higher than the minimum rate (case 3), just as it is slowly decreased in case 1.

It should be noted that as target increases in case 3, (MRCP-target) decreases and rate increases. Eventually the rate-response system may cause the rate to increase above the intrinsic rate and pacing begins—case 1. Now target starts decreasing (case 1), the rate decreases, and eventually the rate falls below the intrinsic rate and case 3 is obtained again. The modes may alternate: for one period of time there is an intrinsic rhythm, then a number of paced beats just slightly faster, then an intrinsic rhythm, etc. Note that as soon as the patient starts to exercise, (MRCP-target) decreases and rate response causes the rate to increase starting just above the intrinsic rhythm—just what is wanted when exercise begins. Also, if the patient's heart stops beating spontaneously, pacing commences near the previous intrinsic rate even though it is higher than the minimum rate.

Alternations of the type described (case 1, case 3) can be avoided (although it is not even necessary to do this). When in mode 3, instead of increasing target every time an MRCP measurement is made, it should not be increased if (MRCP-target) is less than some small limit. This will keep the pacer operating in mode 3 (unless there is a drift, in which case it is desired that target change).

The Calibration Speeds

Figure 18:
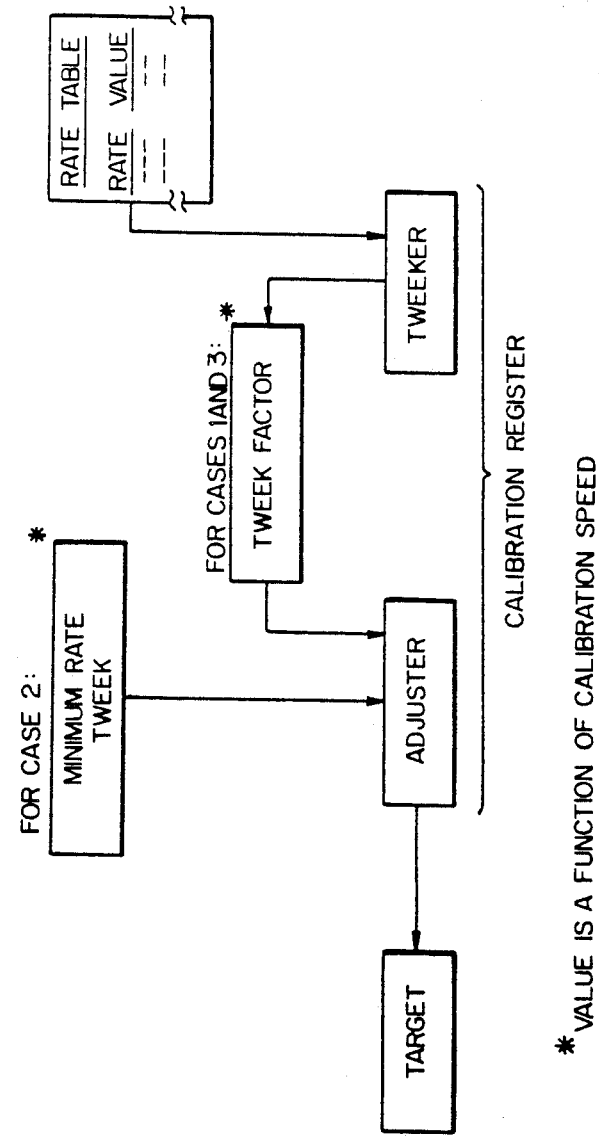
FIG. 18 depicts symbolically the way in which the value of target adjusted in the illustrative embodiment of our invention.

The calibration register which controls changes in target is shown in FIG. 18. The calibration register consists of three registers referred to as the tweeker, the tweek factor and adjuster. The tweeker and the adjuster are 8-bit registers. The tweek factor, used in cases 1 and 3 described in the preceding section, can have a value of 2, 3 or 4. Whenever the tweeker overflows or underflows, the tweek factor is added to or subtracted from the value in the adjuster. Whenever the adjuster overflows or underflows, target is incremented or decremented. The tweek factor is a function of the programmed calibration speed, and the speed at which target is changed thus depends on the calibration speed.

Every fourth beat, when the evoked response is measured, the value in the tweeker register is increased or decreased. This applies only to cases 1 and 3. For case 2, it will be recalled that pacing is at the minimum rate, and target should increase rapidly. The value stored in the minimum rate tweek register is also a function of calibration speed, but it controls much larger adjustments to the value stored in the adjuster register. Thus overflows from the calibration register occur more rapidly, and target is made to increase much faster, than in case 3. The minimum rate tweek is 16 times greater than the tweek factor for any given calibration speed. (Target is increased in case 2 more than 16 times faster than it is in case 3; this is because in case 3 the tweek factor is added to the adjuster register only with an overflow from the tweeker register, while in case 2 the minimum rate tweek is added to the adjuster register in every measurement cycle.)

One complication is that the tweeker value should not be changed by the same absolute amount (a decrease in case 1 and an increase in case 3) independent of the pacing rate. It is desired that target change by a fixed percentage per hour, based solely on the calibration speed and independent of the rate. The faster and pacing, however, the more rapidly MRCP samples are taken and thus the faster the increases and decreases are applied to the tweeker value. It is apparent, therefore, that if target is to change by a fixed percentage over any given period of time, the value by which tweeker is changed whenever an MRCP sample is taken must necessarily vary with the rate at which the samples are taken. [It must be borne in mind that we are not dealing here with changing the tweeker value in accordance with the value of the MRCP. The value of the MRCP is used to control the pacing rate. We are talking here about changing the tweeker value in order to control a change in the value of target, solely to compensate for system drifts. As such, the amount by which tweeker is changed on every fourth beat is a function of rate only and is independent of MRCP.] Toward this end a rate table is provided, as shown symbolically in FIG. 18. A rate of 40 pulses per minute might have a corresponding value of 15, and a rate of 150 pulses per minute might have a corresponding value of 4 in the table. What this means is that the higher rate causes the tweeker value to be changed by a lesser amount each time. Because the rate and value entries in the table have an inverse relationship, the rate at which the tweeker value is changed remains constant over time. [The pacer requires a table to convert between rate and escape interval anyway, the escape interval being an inverse function of the rate. The same table can be used since the same inverse relationship applies to both.]

A slow calibration speed is applicable to an active patient who is not taking any drug therapy (or who may be taking drug therapy, but infrequently (once or twice per day)). For such a patient, target can change by about 10% per hour when the pacer is operating in cases 1 and 3. The medium calibration speed applies to drugs which reach peak serum level over a moderate period of time, i.e., drugs taken every 4–6 hours. This is the default case, and target can change by about 15% per hour. Finally, a fast calibration speed is applicable to a patient who takes drugs which reach peak serum level very quickly, i.e., drugs taken every 2–4 hours. In such a case, target can change by about 20% per hour.

Overdriving In Order To Pace

When the rate-response function is enabled, the pacer measures the RCP every fourth cycle and uses (MRCP-target) to control the pacing rate. The RCP is measured only every fourth cycle in order to save power and increase rate stability. If the present RCP is smaller than target, the rate is increased (5 ppm every fourth cycle) until RCP equals target or the programmed maximum rate is obtained. If the present RCP is greater than target, than the rate is decreased (5 ppm every fourth cycle) until it equals target, or until the programmed minimum rate is obtained.

In the illustrative embodiment of the invention, the RCP is the depolarization gradient of the evoked potential. This means that pacing must occur in order to measure the RCP. If the intrinsic ventricular rate becomes faster than the pacing rate (which pacing rate is established by the RCP measurement), then sensed events will inhibit pacing pulses. (The illustrative embodiment of the invention allows rate response only in the VVI mode.) If there is an intrinsic beat during a cycle in which the RCP is to be measured, the measurement cannot be taken. In order to take a measurement, the pacer increases its rate by 5 ppm every fourth cycle until the intrinsic rate is exceeded and an output pulse is issued. (Although the rate is increased only every fourth cycle in order that there not be too abrupt a change, an attempt is made to measure the RCP during every cycle, rather than just every fourth cycle, in the case of overdrive.)

Once a pacing pulse is generated, a MRCP value is taken and the pacing rate is adjusted accordingly. The adjustment which is made is based on the rate which was in effect prior to the last 5 ppm increase that resulted in a pacer output, i.e., when the pacer rate was within 5 ppm below the intrinsic rate.

There is one complication, however, and that is that an additional 5 ppm decrease in rate is provided in order to allow intrinsic conduction, if still present, to be sensed. This 5 ppm decrease is applied only in the cycle which immediately follows that in which the RCP measurement is taken; it is during this cycle that an extended pacing interval is needed in order to allow sensing of intrinsic conduction if it is present. If intrinsic conduction is sensed, pacer timing is initiated from the sensed intrinsic event and the extended pacing interval is no longer needed.

The reason for this variation can be appreciated by considering a specific example. Suppose that the patient's heart is beating at just above 70 beats per minute, in which case just under 860 milliseconds separate successive atrial beats, and successive ventricular beats. In order to take an MRCP sample, i.e., in order to issue a pacing pulse, it is necessary to increase the pacing rate to 75 ppm, corresponding to an escape interval of 800 milliseconds. There are still 860 milliseconds separating P waves. By decreasing the escape interval to 800 milliseconds during the first cycle which follows sensing of an intrinsic beat, the pacing pulse is 60 milliseconds closer to the next P wave than an intrinsic beat would be were it allowed to occur. Since the P waves are still occurring at the rate of 70 per minute, if the pacing rate is dropped back to 70 ppm immediately following the sensing of an evoked potential with the escape interval now reverting back to 860 milliseconds, the next pacing pulse will be 60 milliseconds closer to the next P wave than it otherwise would be because the preceding pacing pulse was this much closer to the preceding P wave. This might very well mean that a pacing pulse is issued when an intrinsic beat would otherwise be sensed. It is to avoid this situation that the pacing rate is decreased by 5 ppm for a single cycle after the sensing of an evoked potential when the pacer has to overdrive the intrinsic rate in order to take an MRCP sample.

There are three sequences which govern overdrive pacing of this type. The highest rate before overdrive will be referred to herein as the pre-overdrive rate. The three sequences are as follows:

(1) If the RCP measurement indicates that no rate adjustment is necessary (MRCP=target), the pacer initially decreases its rate by 10 ppm for one cycle (5 ppm to compensate for the 5 ppm overdrive, and an extra 5 ppm to allow an intrinsic beat to occur in the next cycle), and then increases its rate by 5 ppm (to cancel the extra 5 ppm) so that the rate is maintained within 5 below the intrinsic rate. [Thus if the pre-overdrive rate was 70 ppm and the rate had to be increased to 75 ppm in order to take a sample, in the cycle following taking of the sample the rate is decreased to 65 ppm, and in the next cycle it is returned to 70 ppm.]

(2) If the RCP measurement indicates that rate should be increased (MRCP is less than target), the pacer initially decreases its rate by only 5 ppm for once cycle, and then increases its rate by 5 ppm in order to return the rate to the value in effect when the overdrive output pulse was issued. In the case of a pre-overdrive pacing rate of 70 ppm, the rate is increased to 75 ppm in order to generate a pacing pulse so that the evoked potential can be sensed. In the next cycle the rate is decreased to 70 ppm, and in the following cycle it is increased to 75 ppm.

(3) If another RCP measurement indicates that a reduction in rate is needed (MRCP is greater than target), the pacing rate is initially decreased by 15 ppm (the additional 5 ppm compared to case (1) is due to the measurement requirement of a rate reduction) and then increased by 5 ppm to bring the rate within 10 ppm below the intrinsic rate. [If the pre-overdrive rate was 70 ppm and the rate was increased to 75 ppm in order to pace the heart, then in the cycle following sensing of the evoked potential the rate is decreased to 60 ppm, and in the next cycle it is increased to 65 ppm.]

Whether rate response is enabled can be programmed by the physician. Two timing cycles with rate response on are illustrated in FIGS. 14 and 15. (Throughout the timing cycle drawings, the darkened area of each cycle depicts the usual refractory period.) The former is a case where overdrive is not necessary. The latter is a case in which intrinsic activity affects the RCP measurement.

As shown in FIG. 14, after the patient starts to exercise, the need to increase the pacing rate is detected in the second cycle when the measured RCP is found to be smaller than target. Between the second and third cycles, the pacer increases its rate by 5 ppm; the escape interval thus decreases by about 57 milliseconds between the second and third cycles. The pacer maintains the rate at this level until the RCP is measured again four cycles later.

During the sixth cycle it is found that the RCP is still smaller than target. The pacer increases its rate once again by 5 ppm, with the escape interval decreasing to 750 milliseconds between the sixth and seventh cycles. The RCP measurement in the tenth cycle indicates that the rate is still not high enough; MRCP is still smaller than target, and the pacer increases its rate once again by 5 ppm with the escape interval dropping to 706 milliseconds.

With cessation of exercise in the eleventh cycle, the need to decrease the rate is reflected in the next RCP measurement at the beginning of the fourteenth cycle. The measured RCP is now found to be larger than target. Therefore, the pacer decreases its rate by 5 ppm, and the escape interval rises to 750 milliseconds between the fourteenth and fifteenth cycles.

The effect of sensing intrinsic activity during rate response is illustrated in FIG. 15. The patient's sinus rate is 71 beats per minute, faster than the initial pacing rate of 70 pulses per minute. At the start of the third cycle an RCP measurement is due, but it cannot be made because the sensed intrinsic activity inhibits the generation of an output pulse. To overcome the intrinsic rate and to allow an output pulse to be issued, the pacing rate increases by 5 ppm between the third and fourth cycles. With the pacing rate increasing from 70 to 75 ppm, the pacing rate is now faster than the intrinsic rates and an output pulse is generated at the start of the fourth cycle. An RCP measurement is now made and it is found that the measured value of RCP is equal to target.

This is an example of the first overdrive case described above: in the cycle following the measurement, the pacing rate is decreased by 10 ppm, and it is then increased by 5 ppm in the next cycle. Thus the V-R interval between beats four and five in FIG. 15 is shown as 890 milliseconds, corresponding to a rate of 67 ppm. The R-R interval during the next cycle is 845 milliseconds, corresponding to an intrinsic rate of 71 ppm. The pacing rate is maintained at 70 ppm, within 5 ppm of the intrinsic rate. The next RCP measurement which is due in the seventh cycle (four cycles after the initial RCP measurement attempt was made, not four cycles after success was achieved), cannot be taken because intrinsic activity is sensed once again. The pacing rate is again increased by 5 ppm between the seventh and eighth beats to allow an RCP measurement to be taken.

Automatic Output Regulation

In order to conserve energy and minimize distortion of MRCP due to lead polarization, the amplitude and width of each output current pulse are preferably such that minimal energy is expended. Toward this end, a threshold search is conducted periodically to determine the pacing threshold. The output values are automatically adjusted accordingly, and a predetermined safety margin is added. Automatic output regulation can be programmed on or off, but when it is programmed on a threshold search is automatically initiated every 54,000 ventricular events; at an average rate of 75 ppm, a threshold search is initiated every twelve hours. Exactly how often the search takes place depends on the pacing rate. A threshold search also occurs upon request by the programmer.

Another aspect of automatic output regulation is capture verification which occurs every four cycles. If loss of capture is detected, it is followed by an adjustment of the output and a verification of capture on a beat-by-beat basis until capture is regained and a predetermined safety margin is added. During every cycle in which loss of capture is detected, a 10-multiampere, 1-millisecond back-up output pulse is issued. Capture verification can result only in an increase of output energy. A decrease can occur only during a threshold search.

It should be noted that if loss of capture occurs during an RCP measurement cycle, then the RCP will appear to be smaller than target, thus causing an increase in rate. Therefore, during lead maturation (when intermittent loss of capture due to lead dislodgment most frequently occurs), automatic output regulation should be programmed on if rate response is programmed on. This allows the automatic output regulation function to detect the loss of capture; rate response is suspended, as will become apparent below, until capture is regained.

During automatic output regulation (both threshold searches and capture verification), output values are increased according to the horizontal steps listed in the table of FIG. 11. The starting pulse width, a programmed parameter, is one of five possible values. Each output incremental step includes both a current amplitude and a pulse width. For example, with a starting pulse width of 0.4 milliseconds, the lowest energy output pulse has an amplitude of 1 milliampere and a pulse width of 0.4 milliseconds. For any starting pulse width, the incremental steps follow first a vertical and then a horizontal line. Thus in the case under consideration, the starting pulse width remains the same but the current amplitude increases up to 5 milliamperes. Thereafter, the current amplitude remains at 5 milliamperes while the pulse width increases in 0.1-millisecond steps up to the maximum of 1.0 milliseconds.

Figure 12:
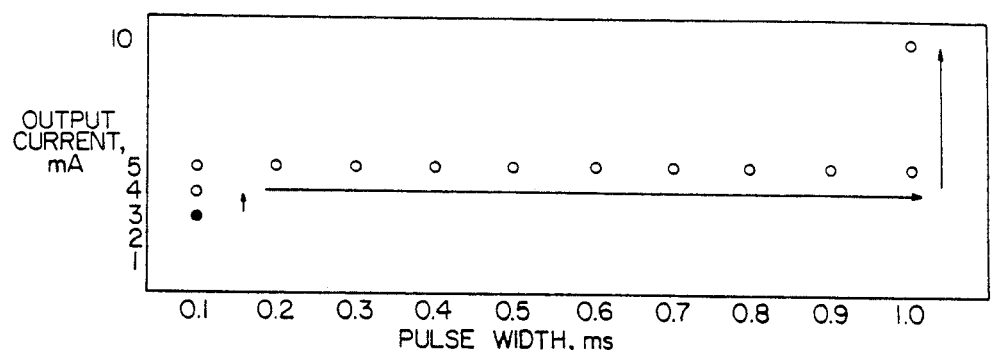
FIGS. 12 and 13 depict two examples of the way in which the table of FIG. 11 is used.
Figure 13:
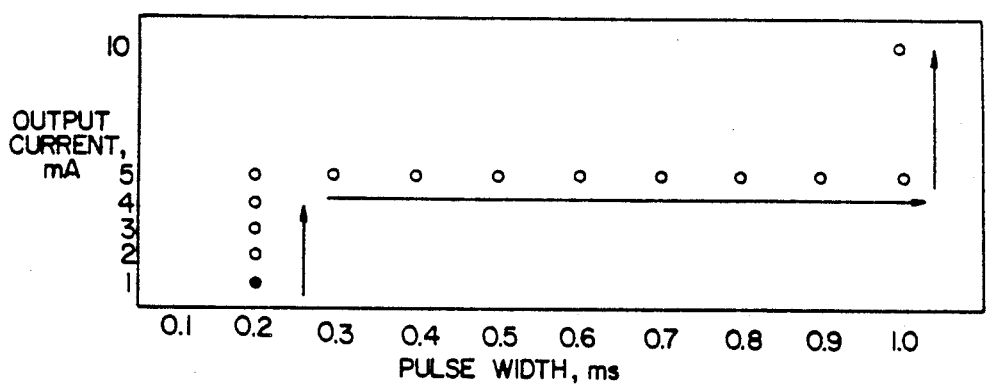

What is shown in FIG. 12 is an illustration of how the pacer changes the output pulse in order to regain capture when loss of capture is detected at an output setting of 3 milliamperes and 0.1 milliseconds. The pulse width is first maintained constant until the output current amplitude is increased to 5 milliamperes. Then the current amplitude remains constant as the pulse width is increased. As will be described below, after capture is verified once again, the output values are increased by two steps in order to provide a safety margin. If the output values reach 5 mA/1.0 ms without capture being regained, or if capture is regained but when the threshold has the safety margin added to it the values exceed 5 mA/1.0 ms, the pacer automatically initiates Stat Set pacing at 10 mA/1.0 ms.

Another sequence is illustrated in FIG. 11, this one representing a threshold search with a starting pulse width of 0.2 ms. During a threshold search the initial current amplitude is always 1 mA. The first four incremental steps involve increasing the current amplitude while maintaining the pulse width at the programmed starting value. Thereafter, it is the pulse width which is incremented. Once again, if the threshold plus safety margin values exceeds 5 mA/1.0 ms, the pacer automatically initiates Stat Set pacing at 10 mA/1.0 ms.

There are two cases of automatic output regulation which must be considered, capture verification and threshold search.

Capture Verification

Capture verification occurs every fourth cycle (when intrinsic beats are not in control). Thus when automatic output regulation is programmed on, loss of capture cannot occur for more than three consecutive cycles without a back-up pulse being issued. If rate response is also programmed on, capture verification occurs in conjunction with the RCP measurements, during every fourth cycle.

Once loss of capture is detected, the pacer performs capture verification during each succeeding cycle, not every fourth cycle, until capture is regained and the new output values have been determined. The pacer verifies cardiac capture through detection of an evoked response following the generation of a pacing pulse. Loss of capture is defined by an evoked response not being detected within 60 milliseconds following an output pulse. When loss of capture is detected, the pacer issues a back-up pulse (10 mA/1.0 ms) 60 milliseconds after the initial output pulse; a primary purpose of the back-up pulse is to insure that there is a beat. The loss of capture results in rate response being suspended; also, the present pacing rate is increased by 5 ppm in order to eliminate possible fusion beats. (Fusion beats make capture verification very difficult.)

If loss of capture is detected in the next pacing cycle, the back-up output pulse is again issued 60 milliseconds after the ordinary pacing pulse, and the pacing rate is again increased by 5 ppm. The total increase of 10 ppm above the rate in effect when loss of capture was detected is designed to eliminate fusion beats if that is what was occurring.

If capture is detected during either of the two cycles following the cycle in which loss of capture was detected, then rate response is resumed, an RCP measurement is taken, and the rate is adjusted accordingly. But if capture is not detected in either of these two cycles, the output values are increased by one step each cycle until capture is detected. Pacing is maintained at the elevated rate of 10 ppm over the rate in effect when loss of capture was first detected until capture verification is complete.

Once capture is regained, the output values are kept constant until capture is verified for three consecutive cycles. Then the pacer issues an ECG "signature" which consists of two output pulses, each at 10 mA/1.0 ms, 60 milliseconds apart. The ECG signature indicates that capture has been regained. The purpose of the signature pulses is to avoid confusion on the part of a person analyzing an ECG trace. Once capture has been verified, the output values are incremented by two steps to establish a safety margin. As mentioned above, if with the safety margin the maximum output values for evoked response detection (5 mA/1.0 ms) would be exceeded, Stat Set pacing is initiated (10 mA/1.0 ms) and automatic output regulation is disabled. Automatic output regulation resumes only if the automatic output regulation is programmed on once again. With Stat Set pacing, rate response is also disabled, if it was programmed on in the first place. The reason for this is that the evoked potential waveform is distorted by large-magnitude Stat Set pacing pulses.

If capture is regained, the new output values (threshold plus safety margin) are first reflected in the cycle following the ECG signature, and they remain in effect until the threshold search is initiated again or loss of capture is again detected for three consecutive cycles. If rate response is programmed on, the pacer resumes rate response once the new output values are determined. If rate response has been programmed off, the pacer returns to the programmed minimum rate in the cycle following the ECG signature cycle.

With respect to increasing the rate in order to avoid fusion beats, the rate cannot exceed the programmed maximum rate, if rate response is programmed on. If rate response is programmed off, the rate cannot exceed 100 ppm, or 15 ppm plus the programmed minimum rate, whichever is greater. (This is the definition of maximum rate in this case.) Whenever the rate has been increased to its maximum allowable level, capture verification continues but rate increases are not allowed.

The capture verification function is illustrated in FIG. 16. In the second cycle, an evoked response is not detected during the 60-millisecond capture verification window which follows the initial output pulse. This causes a back-up output pulse (10 mA/1.0 ms) to be issued 60 milliseconds after the ordinary pacing pulse. The refractory interval is reinitiated. In order to avoid fusion beats if that was the problem, the rate is increased by 5 ppm, with the escape interval thus decreasing from 857 milliseconds to 800 milliseconds. If rate response was programmed on, it is suspended as soon as loss of capture is detected.

In the third cycle, the ordinary output pulse again fails to obtain capture. A back-up pulse is issued, the refractory interval is re-initiated, and the rate is again increased by 5 ppm. In the fourth cycle, failure to obtain capture is detected for the third consecutive time. After the back-up pulse is issued and the refractory interval is reinitiated, the output values, which initially are 4 mA and 0.2 ms, are increased one step to 5 mA/0.2 ms (see table of FIG. 11, row 2, column 4).

In the fifth cycle, the increase in output results in capture by the ordinary output pulse. The present output values of 5 mA/0.2 ms continue to achieve capture in the next two cycles. Because capture is verified for three consecutive cycles (cycles 5, 6 and 7), an ECG signature is issued in the eighth cycle, two output pulses, each at 10 mA/1.0 ms, 60 milliseconds apart.

The establishment of a safety margin is reflected in the ninth cycle. The safety margin is an increase in output by two steps, in this case from 5 mA/0.2 ms to 5 mA/0.4 ms. Capture verification at the new output values continues in cycles 9, 10 and 11. In the twelfth cycle, rate response is resumed, the RCP is measured, and the pacer adjusts its rate accordingly. Thereafter, RCP measurements and capture verification occur every fourth cycle.

Threshold Search

When automatic output regulation is first programmed on, a threshold search is initiated to determine the pacing threshold and to automatically set the output parameter values accordingly. (This includes the usual safety margin of two steps.) After the initial determination, the threshold search is performed automatically approximately every twelve hours, and whenever it is initiated by the programmer.

When the threshold search is initiated, the ECG signature is issued. The pacer increases its present rate by 5 ppm, suspends rate response, lowers the output current to 1 mA, and sets the pulse width to the selected programmed starting value. The current is lowered to 1 mA because the object of the threshold search is to use the lowest possible current amplitude. If capture is not obtained at the lowest output settings, a back-up output pulse is issued 60 milliseconds after the initial output pulse. The pacing rate is again increased by 5 ppm and the output current is increased to 2 mA. If capture is not obtained at these output settings, a back-up pulse is issued and the output current is increased by 1 mA (up to a maximum of 5 mA) each cycle until capture is obtained. (There are not more rate increases, however.) The pacing rate is maintained at the elevated level (10 ppm above the rate in effect when the threshold search was initiated) until the threshold search is completed. If capture cannot be obtained at 5 mA and the starting pulse width value, the pacer increases the pulse width by 0.1 ms (up to a maximum of 1.0 ms) every cycle until capture is obtained. Back-up pulses continue to be issued in each cycle in which capture is not obtained. It will be apparent that the threshold search sequence is very similar to the capture verification sequence, with the major difference being that the capture verification sequence begins with the present output values of current amplitude and pulse width, whereas the threshold search always begins with the lowest possible current amplitude and the programmed starting pulse width.

Once capture is obtained, the output values are kept constant until capture is verified for three consecutive cycles. An ECG signature is then issued to indicate the end of the threshold search, and the pacer increases its output values by two steps to establish a safety margin. Once again, if the two steps take the output values beyond 5 mA/1.0 ms, Stat Set pacing takes place (fixed rate at 70 ppm, with pulses having the back-up output values).

Following capture, the new output values (with safety margin) are first reflected in the cycle following the ECG signature and remain in effect until the next threshold search is initiated or loss of capture is detected for three consecutive cycles. The pacer resumes rate response, measures the RCP, and adjusts its rate accordingly in the fourth cycle following the ECG signature cycle. If rate response has been programmed off, the pacer returns to the programmed minimum rate in the cycle following the ECG signature cycle.

If intrinsic activity is sensed during the threshold search, the search is temporarily suspended and the pacer increases its rate by 5 ppm each cycle until a pacer output pulse is issued. The reason for this is that a threshold search cannot possible be conducted in the absence of pacing pulses. Once pacing starts to take place, the threshold search is continued at the rate in effect when pacing pulses started to be issued.

While the rate is being increased automatically in this manner, it is not allowed to exceed the programmed maximum rate, if rate response is on. If rate response is off, the rate is not allowed to exceed 100 ppm, or 15 ppm plus the programmed minimum rate, whichever is greater. If the rate is increased to its maximum allowable level, the threshold search will continue as long as pacing is in effect, but further rate increases are not allowed. If there are 25 cycles of intrinsic beats or noise beyond the allowable threshold, the threshold search is canceled, rate response is resumed (or the pacer returns to the programmed minimum rate if rate response is off), and the output returns to the values that were in effect when the search was initiated.

The threshold search function is illustrated in FIG. 17. In the second cycle, the ECG signature of two output pulses, at 10 mA/1.0 ms, issued 60 milliseconds apart, indicates the initiation of a threshold search. The present pacing rate is increased by 5 ppm and rate response is suspended, assuming that it was programmed on in the first place.

In the next cycle, an output pulse is issued at the lowest output current value, 1 mA, and the selected starting pulse width value, in this case an assumed value of 0.2 ms. This output pulse fails to obtain capture and a back-up output pulse of 10 mA/1.0 ms is issued 60 milliseconds after the initial output pulse. The refractory interval is re-initiated, the rate is increased by 5 ppm, and the output values are increased by one step, from 1 mA/0.2 ms to 2 mA/0.2 ms.

In the fourth cycle, the output pulse issued at 2 mA/0.2 ms also fails to obtain capture and a back-up output pulse is issued 60 milliseconds after the initial output pulse. The rate remains at the elevated level of 10 ppm above the rate which was in effect when the search was started, and the output values are increased by one step. The new output pulse, issued in the fifth cycle, is shown as succeeded in obtaining capture.

The output values are maintained at the 3 mA/0.2 ms setting until capture is verified for three consecutive cycles, the fifth, sixth and seventh. Then an ECG signature is issued in the eighth cycle to indicate the end of the threshold search. The establishment of a safety margin (output values increased by two steps, from 3 mA/0.2 ms to 5 mA/0.2 ms) is reflected in the ninth cycle. In the twelfth cycle, rate response is resumed, the RCP is measured, and the pacer rate is adjusted accordingly. Thereafter, RCP measurements and capture verification occur every fourth cycle.

Threshold Search High-Level Flow Chart—FIG. 29

The flow chart of FIGS. 19–28 is very detailed and will be described below. At this point it will be useful to consider the flow chart of FIG. 29, however, for two reasons. First, it represents the threshold search which has just been described and accordingly a consideration of the flow chart at this time will help in the understanding of the threshold search. The second reason for considering the flow chart of FIG. 29 is to gain an appreciation of the difference in levels of flow charts such as that of FIG. 29 and that of FIGS. 19–28. The flow chart of FIG. 29 includes a step such as "capture verified three times?". The actual programming of a pacer may entail repetition of the same basic loop over and over again, with different steps being executed each time depending on what transpired during the preceding loops. Yet what is often necessary for an understanding of the functional pacing steps is not what goes on during each pass through the loop, but rather what is going on in terms of pacing functions. It is often easier to understand a system operation in terms of higher level functional steps then it is in terms of lower level operational steps.

Referring to FIG. 29, whenever a threshold search is to be conducted, rate response is first disabled. The ECG signature is then generated, and the starting output values for a pacing pulse are set (1 mA and programmed starting pulse width). The rate is increased by 5 ppm to give precedence to paced events over intrinsic events.

A test is then made to determine whether there have been 25 beats of noise or intrinsic activity during the search. If the answer is in the affirmative, the threshold search is aborted. The output values (amplitude and pulse width) are returned to the previous values. If rate response is off, rate returns to the minimum rate. Rate response is then enabled if it has been programmed on, and an exit is made from the routine.

On the other hand, if there have not been 25 beats of noise or intrinsic activity, a check is made for an intrinsic R wave. What this means is that the pacer waits until expiration of the escape interval and generates a pacing pulse, if an intrinsic R wave is not detected. However, if an intrinsic R wave is sensed, no output pulse is generated. Instead, a check is first made to see if the current rate is equal to the maximum rate. [The test whether rate is equal to the maximum rate only applies if rate response is on. If rate response is programmed off, the rate cannot exceed 100 ppm, or 15 ppm above the minimum rate, whichever is greater.] If it is not, the rate is increased 5 ppm in an attempt to control pacing so that the threshold search can be conducted. If the rate is already at the maximum rate, however, the rate is not increased. This process continues until the rate is high enough to allow an output to be generated. The pacer then checks whether that pulse captures the heart.

In the absence of capture, a back-up pulse is generated after 60 milliseconds to insure that the patient is supported. It will be recalled that the rate is increased by a total of 10 ppm at the start of the threshold search in order to minimize the incidence of fusion beats. If the present output has an amplitude of 1 milliampere, it is an indication that the first pulse in the search has been generated. The rate is increased by another 5 ppm, for a total of 10. During the next pass through the loop, the output amplitude will not be 1 milliampere, and another rate increase will not take place.

It is now that the output values are increased by one step. Recalling that the sequence of increases is such that the amplitude increases to the maximum of 5 milliamperes before the pulse width increases, a test is made to see if the amplitude is less than 5 milliamperes. If it is, the current amplitude is incremented. A return is then made to the top of the main processing loop, to the beginning of a new cycle.

On the other hand, if the current amplitude is 5 milliamperes, the next step must take place in the pulse width. If the pulse width is less than 0.8 milliseconds, the pulse width is increased by 0.1 milliseconds, and a return is made to the top of the loop.

If the pulse width is 0.8 milliseconds, however, it is assumed that capture cannot be obtained at less than the maximum pulse energy. Accordingly, the amplitude is set at 10 milliamperes and the pulse width is set at 1 millisecond. In such a case, Stat Set pacing takes place so the rate is set to 70 ppm (the new minimum rate), and the loop is exited. It should be noted that rate response is not enabled since rate response measurements are not considered valid when the pacing pulses have maximum energy.

The above discussion assumed that capture was not obtained. If capture is detected, the next test is to see whether capture has not only been verified this time through the loop, but whether it has been verified for a total of three times. Capture is verified three times to insure that a reliable threshold has been determined and to reduce the possibility of fusion beats causing a false indication of capture threshold. If the answer is in the negative, a return is made to the top of the loop without the output being increased in energy. The output will be increased once again only if capture is not verified during a cycle before three successive captures take place.

If capture is verified three times in succession, the threshold has been determined. The output is incremented by two steps as a safety margin, and the signature is generated. A test is now made to see whether rate response has been programmed on. If it has not, the rate is set to the minimum rate and the loop is exited. Otherwise, rate response is enabled before exiting the threshold search.

There is one more step indicated at the bottom of the flow chart prior to enabling rate response, and that is that the RCP sample time is determined if rate response has been programmed on. The depolarization gradient is processed twice during each cycle when it is examined. First, it is checked 60 milliseconds after the generation of an output pulse to see whether there has been capture, i.e., whether the depolarization gradient has a sufficient amplitude to indicate capture. But this is not the amplitude which is used as the MRCP. The MRCP is the maximum amplitude depicted in FIG. 6. It is possible to continuously sample the depolarization gradient, at 2-millisecond intervals, for example, for perhaps 130 milliseconds after the generation of an output pulse in order to see where the maximum occurs, and to use that maximum as the MRCP. But taking so many samples during each cycle would require the expenditure of considerable energy. Rather than do this, after the threshold search it is determined when during each of two cycles the peak of the depolarization gradient occurs. The MRCP is measured only at this time during each subsequent cycle in which a measurement is taken.

The MRCP sample us taken somewhere between 70 and 130 milliseconds following the generation of an output pulse. During the two cycles following the threshold search, the depolarization gradient is measured every 2 milliseconds, starting with 70 milliseconds subsequent to the generation of an output pulse. Suppose that the peak value is obtained 90 milliseconds following the generation of the output pulse. In such a case, during every cycle when an MRCP sample is taken, the depolarization gradient is examined only twice—60 milliseconds after the generation of the output pulse to see if the magnitude is sufficient to represent an evoked response, and 90 milliseconds after the generation of the output pulse when the maximum value is expected. (The value at 90 milliseconds is not used to determine whether there has been an evoked response because it is desired to generate a back-up pulse, if one is needed, no later than 60 milliseconds after the generation of an output pulse.)

Target Initialization—FIG. 30

The high-level flow chart of FIG. 30 depicts a target initialization procedure. The detailed steps required for the initialization process are not shown in the low-level flow chart of FIGS. 19–28. The reason for this is that once it is understood how the high-level steps such as those involved in the threshold search of FIG. 29 can be implemented in a low-level detailed flow chart such as that of FIGS. 19–28, it will be apparent to those skilled in the art how to similarly implement the steps in the high-level initialization flow chart.

The three rules which are used to adjust target were described above. A value of target is first determined by the initialization process, a process which is automatically activated when rate response is programmed on. (Target initialization also occurs when a new minimum rate, output current or pulse width is programmed, or when automatic output regulation is programmed on or off while rate response is on.) It is thereafter that the pacer continuously makes adjustments to the value of target in accordance with the three rules which comprise the target-adjustment algorithm. The initialization process is shown in FIG. 30.

The initial value of target should be determined while the patient is at rest, i.e., when the RCP is not being affected by emotional or physical stress. If initialization is performed while the patient is under emotional or physical stress, the target RCP will be established at too low a level and may not allow an appropriate rate response. However, the effect is only temporary because the automatic calibration function eventually adjusts target to the appropriate minimum-rate level. For that matter, target will eventually be adjusted correctly even in the absence of an initialization process.

During initialization, the RCP is measured for a number of paced cycles in order to establish a value for target. If intrinsic activity is sensed during the initialization process, initialization is temporarily suspended and the rate is increased by 5 ppm every cycle until pacing resumes.

The first test which is made is to see whether intrinisic R waves are being sensed. As indicated at the top of the flow chart, if an intrinsic beat takes place, the rate is increased by 5 ppm unless the rate is already at the maximum. (Maximum rate in the flow chart of FIG. 30 has the same meaning as maximum rate in the flow chart of FIG. 29.) Only if a paced beat takes place does the system move on to determine the RCP sample time as indicated in the flow chart.

The actual determination of the RCP sample time is the same as that discussed above in connection with the flow chart of FIG. 29. The depolarization gradient is examined every 2 milliseconds until it is determined when following an output pulse a maximum value is obtained. Thereafter, that is the RCP sample time.

In connection with both FIGS. 29 and 30, two measurements are actually taken in order to determine the RCP sample time. In this regard, it will be helpful first to consider the next sequence in the flow chart of FIG. 30, the determination of an initial value of RCP. As shown in the flow chart, after the RCP sample time is determined, a measurement is taken of the RCP. The latest RCP value is subtracted from the preceding value, and the difference is examined. If the difference is not large, it is assumed that the two measurements have validity and the processing proceeds. On the other hand, if the difference exceeds a threshold value (determined by the particular measurement system involved), another RCP value is taken. In all cases, the most recent value is subtracted from the preceding one, until two successive values which are approximately equal are obtained. The most recent of those two samples is taken as the applicable RCP value.

In exactly the same way, the RCP sample time is determined, although it is indicated as only one step in each of FIGS. 29 and 30. Successive RCP sample times are determined until two successive measured values are close enough together for it to be assumed that a sufficient level of accuracy has been achieved. The most recent of the two values is taken as the RCP sample time.

Returning to the flow chart of FIG. 30, at least four cycles are required to determine the RCP sample time and to determine an initial value of RCP. During the next 16 paced cycles, RCP measurements are taken. It should be noted that to speed up the initialization process, samples are taken every cycle, not every fourth cycle. Furthermore, target is calibrated at an accelerated speed. The calibration speed is that applicable to Rule 2, rather than that applicable to Rules 1 and 3.

Any measurement system necessarily has a range outside of which values are not considered to be accurate. If during the derivation of target the measured RCP is not out of range, a double pulse signature is generated, and rate response is enabled.

On the other hand, if the target RCP is out of range, a status flag is set to indicate this condition. The status flag allows the RCP out-of-range condition to be telemetered out to a programmer. With the RCP out of range, Stat Set pacing takes place, as indicated at the bottom of FIG. 30. Rate response is not enabled (nor is automatic output regulation).

Detailed Flow Chart—FIGS. 19–28

Figure 19:
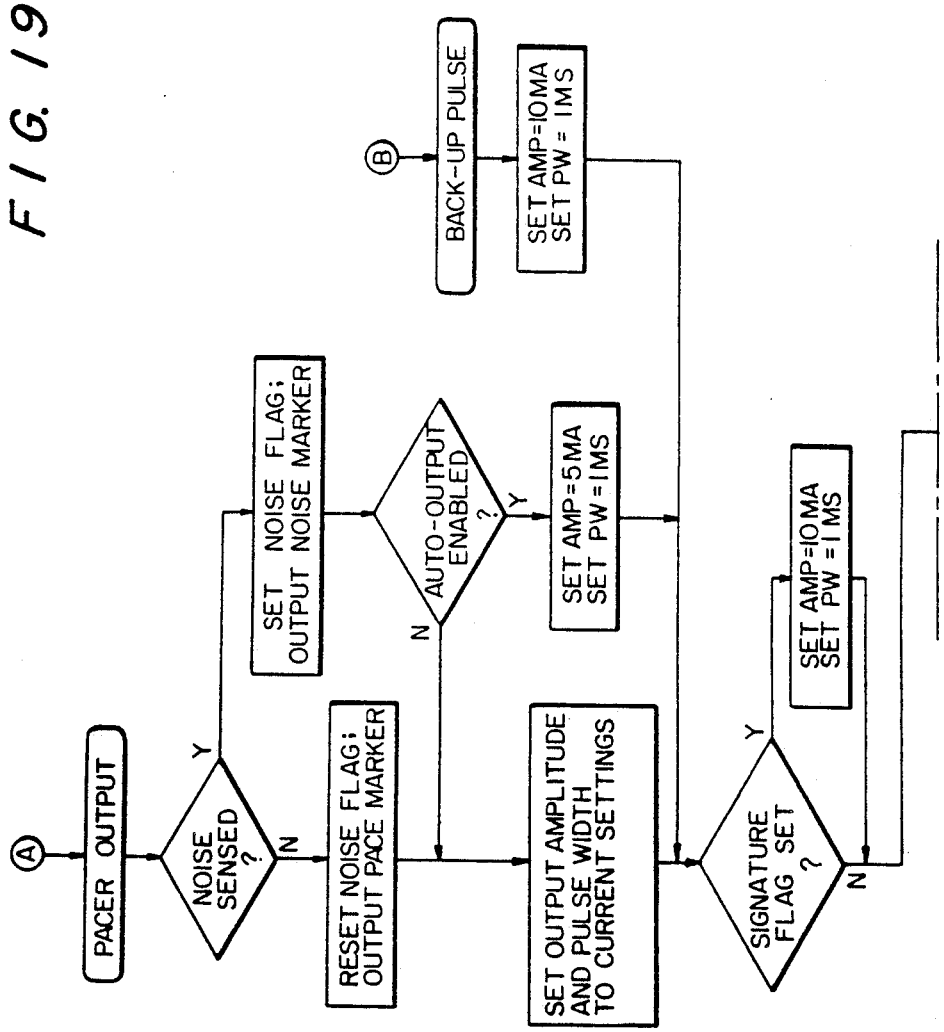

The pacer output module heading block shown at the top of FIG. 19 is entered from those parts of the flow chart labeled A, as will be described below. The pacer output module is entered when a spontaneous beat has not been sensed and a stimulus is to be issued. It is not certain, however, that there has been no intrinsic beat. It is possible that there was an intrinsic beat, but that it was masked by noise. It is for this reason that the first test which is performed is to determine whether noise was sensed during the preceding cycle.

If it was, a noise flag is set and a noise marker is output by the telemetry circuit. Three markers can be output for recording on an ECG trace. The markers represent an output pacing pulse, noise and a sensed event. If it is determined that noise was not sensed during the preceding cycle, then as indicated in FIG. 19 the noise flag is reset. Instead of outputting a noise marker, a pace marker is generated in anticipation of the pacing pulse which is about to be issued.

If a pacing pulse is applied to refractory tissue, an evoked potential will not be sensed and it is possible for the pacer to think that there has been a loss of capture when in fact there has been no such thing. To avoid this, when noise is sensed capture detection and automatic output regulation are suspended. (That is why the noise flag is set, as will become apparent below.) Instead, pacing takes place with the largest possible output which does not distort the evoked response to the point at which the RCP cannot be measured accurately. (RCP measurements are taken even in the presence of noise.) Consequently, as indicated on FIG. 19, if automatic output regulation has been enabled, the output amplitude is set at 5 milliamperes and the pulse width is set at 1 millisecond. On the other hand, if automatic output regulation has not been enabled, then the output amplitude and the pulse width are set to whatever settings have been programmed by the physician. Similarly, in the absence of noise, the current settings—whether set by the physician in the absence of automatic output regulation, or automatically determined if automatic regulation has been enabled—are used to generate the pulse.

As will be described below, there are several points in the flow chart at which it is determined that it is necessary to generate a back-up pulse. These points are indicated by the letter B. As shown in FIG. 19, the back-up pulse module heading block is entered at such a point in the flow chart, at which time the output amplitude is set at 10 milliamperes and the pulse width is set at 1 millisecond.

As will become apparent below, there are several points in the program at which it is determined that it is necessary to generate an ECG signature—two pulses, 60 milliseconds apart, each having an amplitude of 10 milliamperes and a pulse width of 1 millisecond. Before the output pulse is actually generated, the signature flag is examined to see if it is set. If it is, the back-up pulse output values are set even if other output value settings were previously established.

Figure 20:
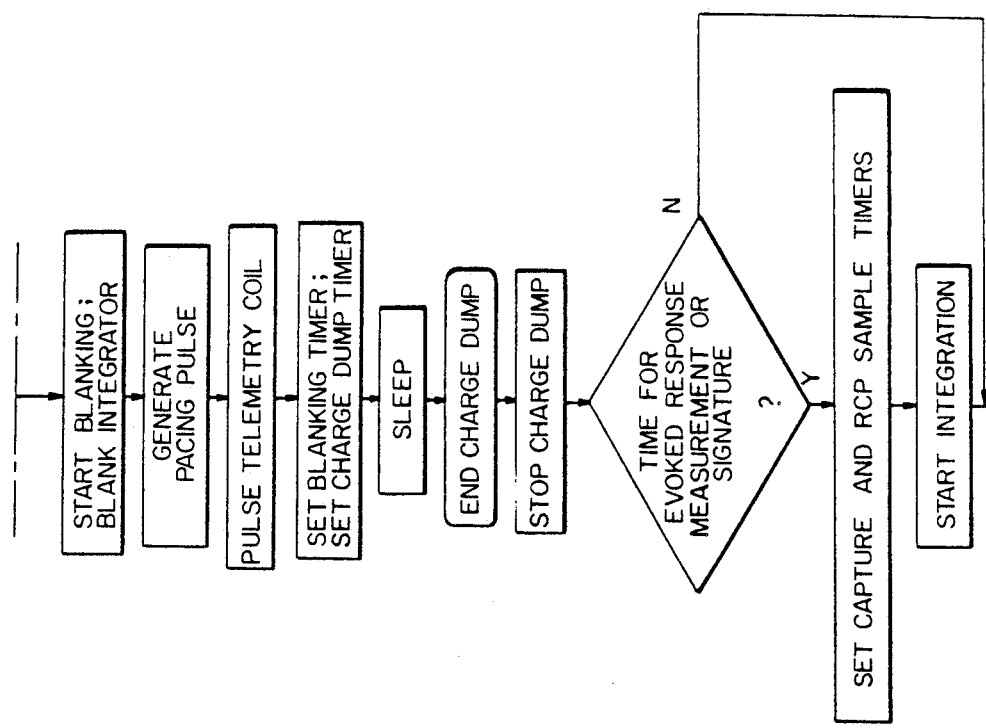

The flow chart proceeds to the top of FIG. 20 at which point blanking is started. This is the conventional step by which the sense amplifier is protected from large pulses. Because the system of the invention also includes an integrator (see FIG. 7) which must be protected, the integrator is also blanked just prior to generation of the pacing pulse. In the next step the pacing pulse is generated.

The third step in FIG. 20 is the pulsing of the telemetry coil. This step has nothing to do with the invention itself. The telemetry coil is pulsed only to tell the programmer that now is an advantageous time to program, if programming is required, because pulsing has just taken place. In some systems programming causes an interruption in sensing/placing, especially if the programming takes longer to complete than the escape interval. The interruption time can be minimized by starting the programming at the beginning of an escape interval.

Two timers are now set. The blanking timer is set at 140 milliseconds; this is the time during which the sensing of intrinsic beats or noise is not allowed. The charge dump timer is set for 10 milliseconds; this is the time during which the charge which is stored in body tissues is dissipated (see top left of FIG. 7).

As is by now standard in the pacing art, the microprocessor is put to "sleep" whenever possible in order to minimize power dissipation. The microprocessor is awakened by the timing out of a timer or, when appropriate, upon the sensing of an event. In the present case, the microprocessor is put to sleep and remains in this state until the first of the two timers times out.

It is the 10-millisecond charge dump timer which times out first, at which time the microprocessor starts to function again and the end charge dump module is entered. The first step which takes place is that the charge dump is stopped. A test is then performed to determine whether it is time for an evoked response measurement or a signature pulse. This step requires explanation because it would appear that there is no connection between the time when an evoked response measurement is necessary and the time when a signature pulse is to be generated.

An evoked response measurement is made every fourth beat, or every beat during initialization and threshold searches. Similarly, evoked response measurements are made when there is a loss of capture, or when there is a fusion beat which might be interpreted as a loss of capture. These various conditions have been described above, and will become apparent below. The important thing is to recognize that evoked response measurements are made twice during a cycle—60 milliseconds after the generation of an output pulse to determine whether the pulse captured the heart, and 70-130 milliseconds after the generation of the pulse when the peak depolarization gradient potential is expected. Toward this end, two timers are set—the capture timer and the RCP sample timer. It will also be recalled that the signature consists of two large-amplitude pulses separated by 60 milliseconds. If the signature flag has been set, one such pulse has already been generated in the second step of FIG. 20. In order to generate the second pulse, the capture timer is set, and the second pulse is generated upon its timeout. It is for this reason that the capture timer is set on what would appear to be either of two disconnected needs—the need to sense an evoked response, or the need for a signature pulse. (If it is a second signature pulse which is required, the RCP sample timer is still set along with the capture timer. Since a measured RCP is not accurate in the presence of a large-amplitude stimulus, the RCP sample timer timeout is ignored, as will become apparent below.)

The capture sample time is 60 milliseconds. However, by the time the capture sample timer is set, 10 milliseconds have already gone by since the generation of the pacing pulse, as a result of the operation of the charge dump timer. Consequently, the capture sample timer is actually set to 50 milliseconds in order to time out a 60-millisecond capture sample interval. In a similar manner, the RCP sample timer is set to 10 milliseconds less than the RCP sample time which is determined during the initialization routine.

It might be thought that an RCP sample alone would suffice; it could not only provide an MRCP value, but it could also serve to verify whether there has been an evoked response. However, if there has not been an evoked response it is desired to issue a back-up pulse to support the patient. Since the RCP sample is taken 70-130 milliseconds after the generation of a stimulus, in the event of a fusion beat, perhaps resulting in an MRCP value too low to be recognized as an evoked response, a back-up pulse issued 70-130 milliseconds after the stimulus might actually fall in the T wave, something which is generally to be avoided. If a back-up pulse is to be issued, it should take place earlier in the cycle when it will not fall in the T wave even if the pacer mistakingly treats a fusion beat as a loss of capture. For this reason a capture sample after 60 milliseconds is also necessary, and two samples must be taken each cycle.

Figure 21:
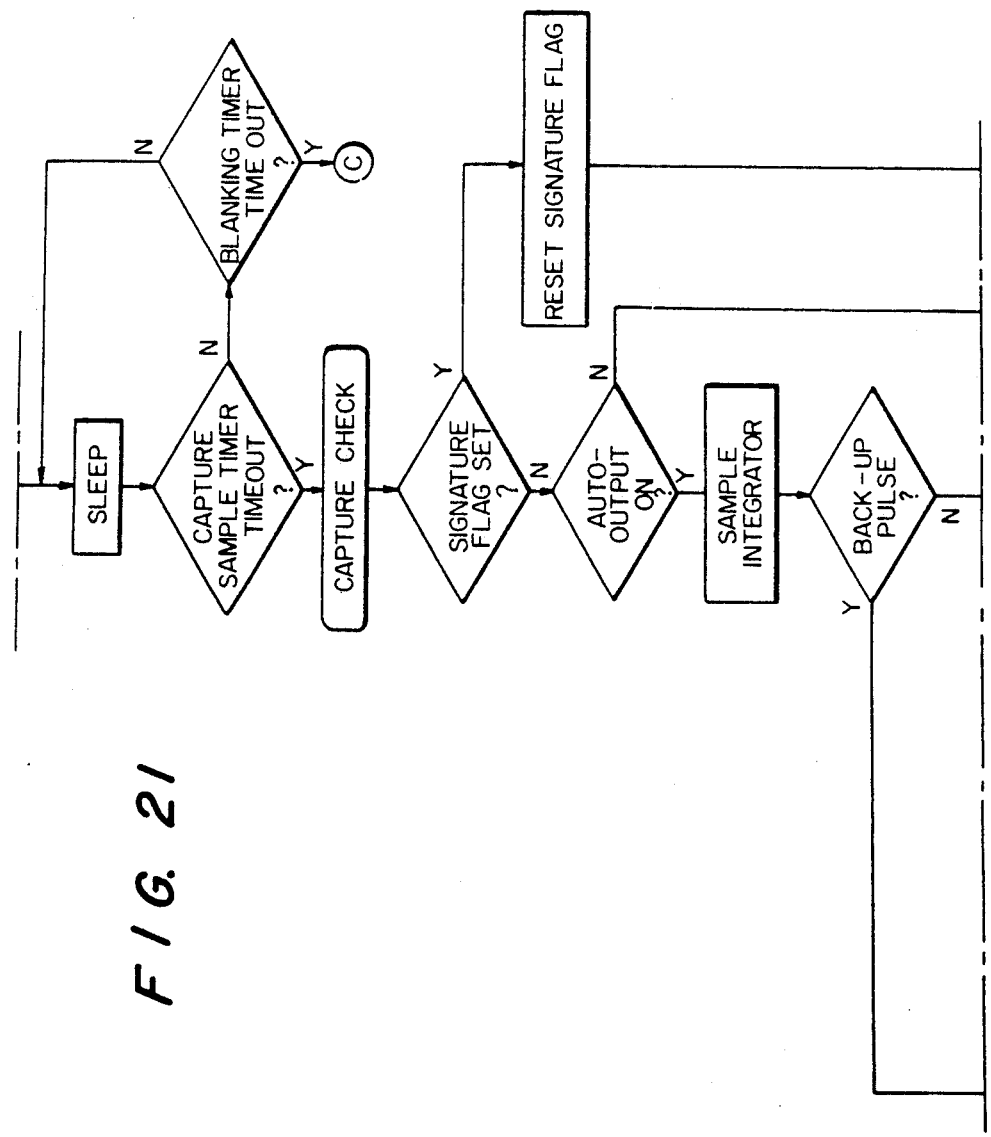

After the capture and RCP sample timers are set, the integrator (FIG. 7) is turned on so that the depolarization gradient will be measured and values will be available on either timer timeout. The system then goes to sleep, as indicated at the top of FIG. 21 until one of the timers times out.

The system then checks whether the capture sample timer has timed out. If not, a check is made whether the blanking timer has timed out. In the event neither timer times out, a pass is made through the loop at the top of FIG. 21 once again. Eventually, one of the timers times out. (Although the capture sample timer has a shorter interval than the blanking timer, the former is usually not set, e.g., on 3 out of 4 cycles, and it is the blanking timer which usually times out.) If it is the capture sample timer which times out, the system moves on to the capture check routing; otherwise, the system moves on to the end blanking routine at the top of FIG. 26. It should be noted that if there is a capture sample timer timeout at the top of FIG. 21, the blanking timer is not ignored. The blanking timer timeout is handled in the end blanking module at the top of FIG. 26.

It will be recalled that the capture sample timer is set not only if an evoked response measurement is necessary, but also if a signature pulse pair is required (see bottom of FIG. 20). The first pulse of the pair is controlled by the test of the signature flag at the bottom of FIG. 19, followed by the generation of a pacing pulse at the top of FIG. 20. The second pulse is controlled by checking the signature flag once again in the middle of FIG. 21. When the capture sample timer times out 60 milliseconds after the first pulse of the pair is generated, another pacing pulse is generated. First the system resets the signature flag since it is no longer needed. Moving on to FIG. 22, a pace marker is outputted because another pacing pulse, the second half of the signature, will be issued. A check is now made to see whether it is time for a rate increase. Referring to the threshold search routine shown on FIG. 29, it will be recalled that at the start of the search, the pacing rate is increased in two steps of 5 ppm each. The purpose of the increase is to minimize the possibility of fusion beats. The first increase takes place when the second signature pulse is issued. There are other times when the rate must be increased, but the only one of concern now is when the second signature pulse is to be issued at the start of a threshold search routine. (The same path through the flow chart is taken when the signature is issued at the end of the threshold search routine; at this time the rate is not increased because there is no reason to do so.) A check is made to see whether the rate is at a maximum and, if it is not, the rate is increased by 5 ppm. Processing then resumes at point B in FIG. 19, where the output parameters are set for actual issuance of the second pulse of the signature pair. The pulse is actually treated as a back-up pulse since they have the same output values.

The way in which the two pulses of the signature pair are generated illustrates the basic difference between the high-level flow chart of FIG. 29 and the detailed flow chart of FIGS. 19–28. At the top of FIG. 29 there is a single step in which the pulse pair of the signature is said to be generated. In actuality, it take two passes through the main processing loop because both pulses are generated in the second step of FIG. 20. The methodology is easier to understand from a high-level flow chart such as that of FIG. 29, although details of implementation must be left to a low-level flow chart.

Returning to FIG. 21, in the usual case, the signature flag set test will be answered in the negative; this point in the main processing loop is usually reached with timeout of the capture sample timer 60 milliseconds after the generation of a non-signature pacing pulse (and usually only on every fourth cycle). A test is then made to see whether automatic output regulation has been programmed on. If it has not, a branch is taken to the middle of FIG. 22 where a test is performed to see whether rate response is enabled. If automatic output regulation is on, on the other hand, a check is now made to see whether there has been an evoked response; this is accomplished by sampling the output of the integrator which represents whether or not there has been capture.

Figure 22:
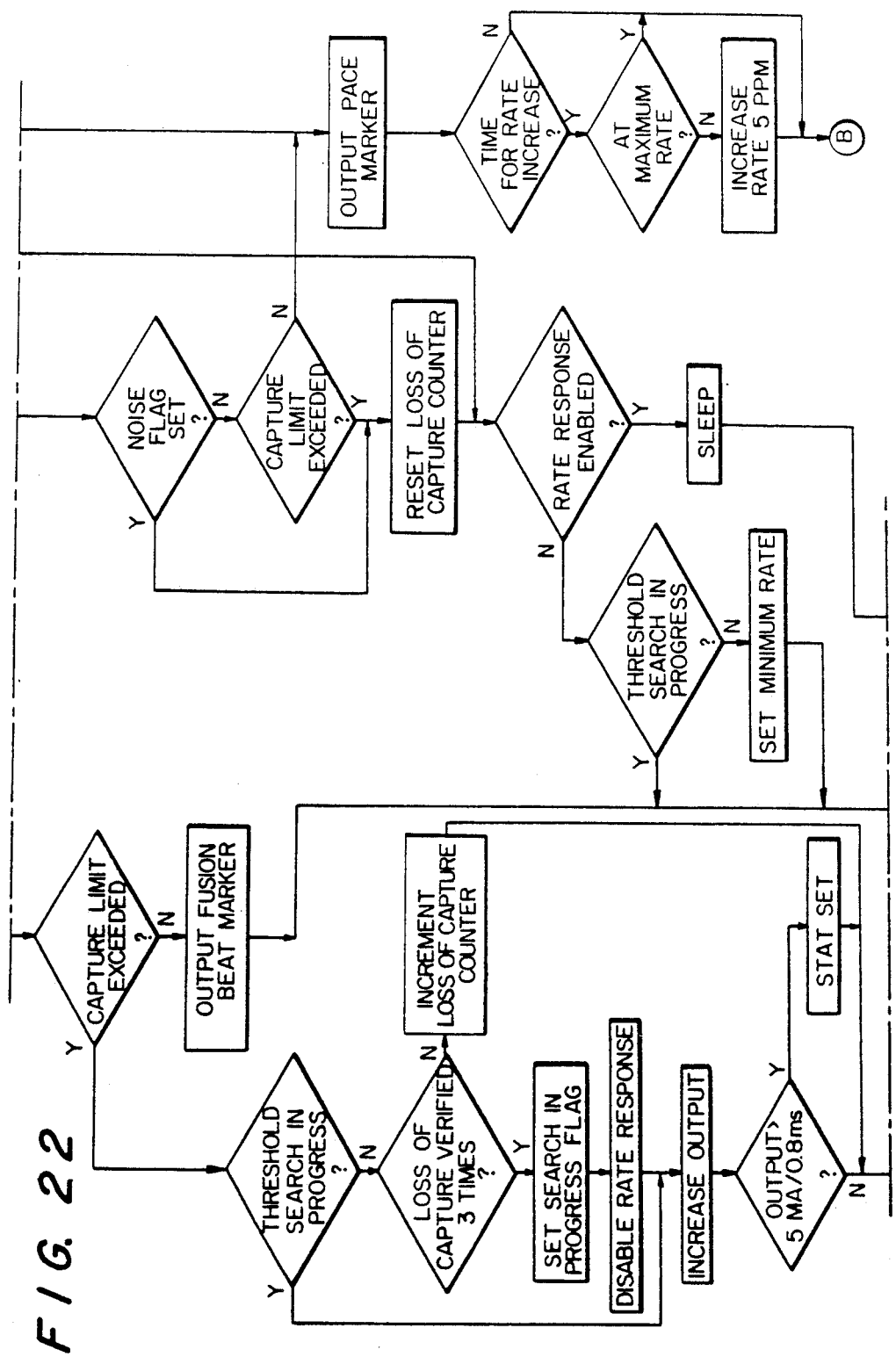

At the bottom of FIG. 21, a branch is taken depending upon whether what has been issued is a back-up pulse. The pacing pulse can be part of the signature, a back-up pulse or an ordinary stimulus. A back-up pulse is generated only when the ordinary stimulus has not captured the heart. Assuming that an ordinary stimulus has been generated, the next test which is performed, at the top of FIG. 22, is to see whether the noise flag has been set. This flag is set at the top of FIG. 19 if noise has been sensed. If noise is present, a test is not made to see whether the capture limit has been exceeded, i.e., whether the stimulus has captured the heart. The reason for this is that the noise may mask what is really going on. As will be described below there is a counter which keeps track of the number of capture failures (loss of capture). That counter is now reset because the count is not reliable in the presence of noise. The system moves on to the rate response routine which begins in the middle of FIG. 22.

On the other hand, if the noise flag is not set, the capture-limit-exceeded test in FIG. 22 is performed. If the capture limit is exceeded, the loss of capture counter is reset; it will become apparent below that the current count is of no importance because capture has been regained. But if the capture limit has not been exceeded, what is required is a back-up pulse since the pacing stimulus has failed to capture the heart. A pace marker is first outputted. The reason for this is that a back-up pacing pulse will be issued momentarily. The system then checks to see whether it is time for a rate increase. The reason for the test here requires careful understanding.

The reason that a stimulus is generated in a fusion beat is that the pacer does not sense the beat, even though it may have just begun. But the remaining question is why the evoked potential may not be sensed 60 milliseconds later. There are two reasons for this. First, the sense signal may be on the decrease by the time 60 milliseconds have elapsed after the output pulse is generated, when the pacer looks to see whether there has been capture; that is because depolarization started early—even before the stimulus. Second, the sense signal for an intrinsic beat is generally narrower than that for a paced beat, so it may be even more difficult to sense capture. Fusion beats may thus be interpreted as a loss of capture. That is why it is a general approach in the invention to increase the pacing rate during automatic output regulation in order to minimize the possibility of fusion beats. However, experiments have actually shown that fusion beats may still occur often enough to be of concern even when the pacing rate is increased by as much as 10 ppm during automatic output regulation. It is for this reason that a unique test has been developed for actually determining whether a fusion beat has occurred, a test which will be described in detail below.

The fact that the capture-limit-exceeded test was answered in the negative does not necessarily mean that the output parameters of the pacing pulse are not sufficient to capture the heart. It is possible that a fusion beat took place, with the result that the capture sample was too low in magnitude to represent capture. Before the system increases the output pulse energy in an attempt to regain capture, it tries to avoid fusion beats in the hope that it will be possible to verify that the present output pulse energy is sufficient. It is for this reason that the pacing rate is increased twice in succession, 5 ppm each time. A back-up pulse is about to be issued since capture may have been lost and the heart may not have beat, but the rate increase is in preparation for the next ordinary stimulus which will be generated. As shown in FIG. 22, the rate is increased by 5 ppm only if the rate is not already at the maximum. A branch is then taken to point B on FIG. 19 at which time a back-up pulse is generated.

Assuming that an ordinary stimulus resulted in the failure of the capture-limit-exceeded test at the top of FIG. 22, a back-up pulse is now generated, as just described. From entry point B on FIG. 19, the system moves on to the steps shown in FIG. 20. There is another charge dump, and the sense amplifier and integrator are both blanked. At the bottom of FIG. 20, the capture and RCP sample timers are set because evoked response measurements are made for back-up pulses. Actually, RCP samples are not taken because they are unreliable with maximum-energy stimuli, but capture samples are taken. On FIG. 21, the auto-output-on test is answered affirmatively because the only time that back-up pulses are generated in the first place is when automatic output regulation has been programmed on. At the bottom of FIG. 21, the back-up pulse test is answered affirmatively, and a branch is taken to the top of the left path on FIG. 22.

On FIG. 20, a test is performed whether it is time for an evoked response measurement. When capture has been lost, a capture sample is taken on all succeeding cycles until the problem is resolved. As just described, an ordinary stimulus results in a pass through the path on the right side of FIG. 22, the rate is increased by 5 ppm and then a back-up pulse is issued. Following the back-up pulse, a pass is made through the left branch on FIG. 22. Then another ordinary stimulus is generated, a pass is made through the right branch (assuming that the capture-limit-exceeded test is failed once again), the rate is increased by another 5 ppm, a second back-up pulse is generated, and a second pass is taken through the left path on FIG. 22. The two 5-ppm increases are designed to eliminate fusion beats if that is the problem. It might be expected that two rate increases in the space of three cycles, would solve the fusion beat problem. We have discovered, however, that the heart can actually exhibit three successive fusion beats, with a 5-bpm rate increase between the first and second, and another 5-bpm increase between the second and third. Each pass through the right path of FIG. 22 can represent a true loss of capture, or it can represent a fusion beat. Increasing the pacing rate even by 10 ppm is not enough to distinguish between the two conditions. It is for this reason that the steps in the left path of FIG. 22 are provided.

As seen at the bottom of FIG. 21, the left path of FIG. 22 is entered following the taking of a capture sample 60 milliseconds after the generation only of a back-up pulse. At the top of FIG. 22, a test is made to see whether the capture limit has been exceeded, i.e., whether the back-up pulse captured the heart. The results of the test are used in a unique way to tell whether what is going on is a true loss of capture or a sequence of fusion beats. Interestingly, capture by a back-up pulse is an indication that what is involved is a loss of capture. This paradox will now be explained.

Each back-up pulse is generated 60 milliseconds after an ordinary stimulus. The question to be answered is whether what appears to have been a loss of capture was really a loss of capture or simply a fusion beat (with the result being that the capture sample was too low in magnitude, as explained above, for the sample to verify capture). If the back-up pulse does not capture the heart now, i.e., the test at the top left of FIG. 22 is answered in the negative, a logical explanation is that capture was not just achieved because the heart tissue is refractory. This in turn means that the heart beat before the back-up pulse was generated. Since an intrinsic beat was not sensed and capture was not verified following generation of the ordinary stimulus, what must have happened is that there was a fusion beat. Consequently, if the back-up pulse does not capture the heart, a fusion beat marker is output. The system then moves on to FIG. 23 where the RCP sample timer is stopped. Because large-magnitude back-up pulses cause the depolarization gradient to be distorted, RCP samples are not taken following the generation of back-up pulses. The microprocessor is then put to sleep and a branch is taken to point C on FIG. 26; the blanking timer was set prior to the generation of the back-up pulse, and the system waits for blanking to end. It should be noted that the rate was increased by at least 5 ppm and by at most 10 ppm by the time the capture-limit-exceeded test at the upper left of FIG. 22 is answered in the negative. The rate is returned as will be described shortly.

On the other hand, suppose that the test at the top left of FIG. 22 is answered affirmatively—the back-up pulse did capture the heart. This means that the heart tissue was not refractory, which in turn means that the heart did not beat just prior to the back-up pulse. This is interpreted as a loss of capture on the part of the preceding ordinary stimulus. The fact that a single pulse may not have captured the heart may or may not be sufficient to control an increase in the output energy. Whether it is depends on whether a threshold hold search is in progress. If the search is already in progress, a single loss of capture is enough to control a step increase in the output energy, as indicated in FIG. 22. A test is then made to see whether the maximum output energy (short of a back-up pulse) has been reached. If it has, the system reverts to Stat Set pacing.

The RCP sample timer is then stopped; the left branch of FIG. 22 is entered because a back-up pulse was generated, and RCP samples are not taken following the generation of back-up pulses. The microprocessor is then put to sleep and processing resumes with the end blanking routine when the blanking timer times out.

The above description assumed that the threshold-search-in-process test on FIG. 22 was answered affirmatively. If a threshold search is not in progress, what it means is that an ordinary stimulus resulted in a loss of capture, as confirmed by a back-up pulse now capturing the heart. A test is made to see whether a loss of capture has occurred three times; this is accomplished by examining the loss of capture counter. (The reason for resetting the loss of capture counter in the step shown in the middle of FIG. 22 in the presence of noise, or following verification of a capture, is that when the loss of capture counter reaches a count of three, the output will be increased until capture is regained, and there is no need for that if capture is regained before a triggering count of three is reached.) If capture failure has not been verified at least three times, the loss of capture counter is incremented, the RCP sample timer is stopped, and the microprocessor is put to sleep until the end of blanking.

On the other hand, if loss of capture has been verified three times, a number of times sufficient to guard against an erroneous determination of loss-of-capture, then what is done is to control an increase in output energy. This is a form of threshold search, except that the starting output energy is the current value. The search is controlled by setting the search-in-progress flag. Rate response is then disabled because it is always disabled when the output pulse energy is in the process of being changed. The output is then increased, following which a test is made to see whether the upper limit has been reached, just as the test is performed during a threshold search. The RCP sample timer is then stopped and the microprocessor is put to sleep until the end of blanking. The next time that the path on the left side of FIG. 22 is entered, the threshold-search in-progress test will be answered affirmatively.

In the middle of FIG. 22, there is a test to see whether rate response has been enabled. At the end of the automatic output regulation routine, whether what has been involved is a periodic threshold search or the routine which follows an apparent loss of capture, the rate may have been increased by 5 ppm or 10 ppm as a result of the effort to avoid fusion beats. This increase should be compensated for. If rate response has been enabled, there is no need to do anything because the rate will be adjusted by the rate response routine to be described below; the artificial increase in rate will be lowered because the rate is too fast for present physiological needs. As shown at the bottom of FIG. 22, the microprocessor is put to sleep and the rate response module is entered. When the RCP sample timer times out 70–130 millisecond after the last stimulus was generated, rate response processing takes place.

On the other hand, if rate response has not been enabled, an adjustment must be made for the 5-ppm or 10-ppm increase in rate which may have taken place. A test is made to see whether a threshold search is in progress. At the end of the threshold search, as will be described below, the search-in-progress flag is reset. If it is reset and the answer to the threshold-search-in-progress test is in the negative, the minimum rate is set (it being recalled that the assumption is that rate response has not been enabled). On the other hand, if a threshold search is in progress, the minimum rate is not set, and the system waits for blanking to end.

Figure 23:
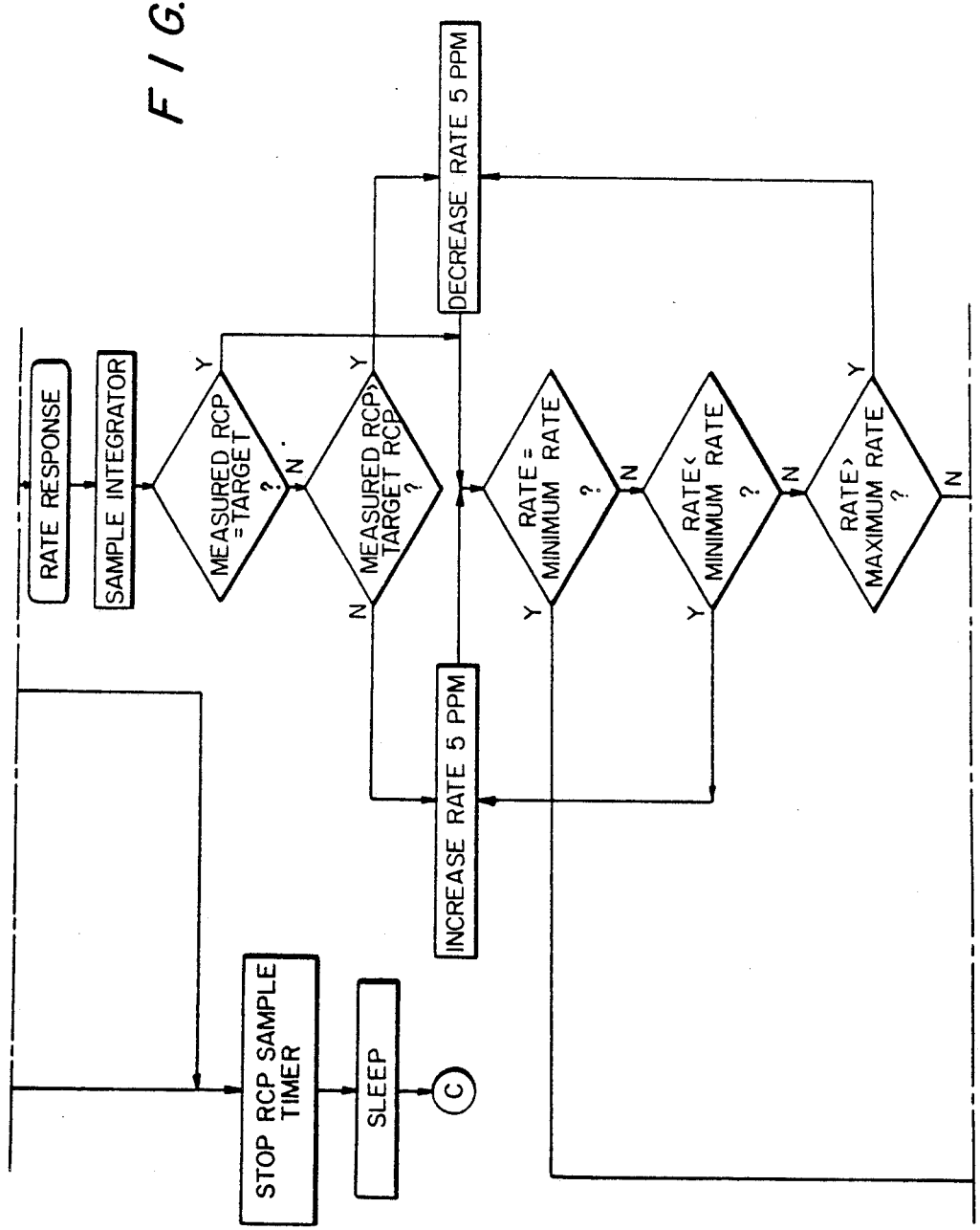

The top (right branch) of FIG. 23 is reached when an RCP sample is to be taken as a result of rate response being enabled and a stimulus having been generated. It is at this point that the rate is adjusted in accordance with the measured value of the RCP, and target is adjusted in accordance with the three Rules enumerated above.

If the measured RCP (MRCP) equals target, then no change in rate is necessary. The control parameter (MRCP-target) is zero, and this means that the present rate is on target. On the other hand, if MRCP does not equal target, a test is performed to see whether the control parameter is positive or negative. A branch is taken to increase the rate by 5 ppm or to decrease it by the same amount. As mentioned above, the advantage of a closed-loop system is that it is not necessary to pre-define what would otherwise be a complex relationship between the control parameter and the rate. All that it is necessary to do is to increase or decrease the rate until the control parameter returns to the desired value.

Whether the rate is increased, decreased or left alone, a test is performed to see if the rate, after any decrease or increase which may have occurred, is equal to the minimum rate. If it is, a branch is taken to the left side of FIG. 23. If the rate is not equal to the minimum rate, two tests are performed to verify that the rate, as it may have been just adjusted, is within the minimum and maximum limits. If the rate is now below the minimum rate, it is increased; if the rate is now above the maximum rate, it is now decreased. After such an increase or decrease, the processing continues at the bottom of FIG. 23, along the left branch if a minimum rate condition has been obtained, or along the right branch if the rate is between the minimum and maximum limits.

If the system is operating at minimum rate, Rule 2 requires that target be increased rapidly. What is required is that target be successively increased until the difference between it and MRCP is less than some minimum limit (which for all intents and purposes means that target and MRCP are equal). The difference between target and MRCP is compared to the RCP limit, and a test is then performed to see if the limit is exceeded. If it is not, target has been sufficiently increased and a branch is taken to the bottom of FIG. 25 where the microprocessor is put to sleep and the system waits for the end of blanking. (It is to be recalled that all of this processing is taking place following the generation of a pacing pulse.)

If the limit is exceeded, then target adjuster is increased. Referring to FIG. 18, for Case 2 the value stored in the minimum rate tweek register is added to the adjuster register. The value stored in the minimum rate tweek register depends on the calibration speed, and it is 16 times larger than the tweek factor. This is not to say that Rule 2 results in the increase of target at a rate which is only 16 times faster than the rate at which target is increased or decreased in Case 1 and 3. That is because the only time that the tweek factor is added to or subtracted from the adjuster register is when there is an overflow or underflow from the tweeker register. Thus target is increased in Case 2 much faster than just 16 times relative to the speeds in Cases 1 and 3.

Figure 24:
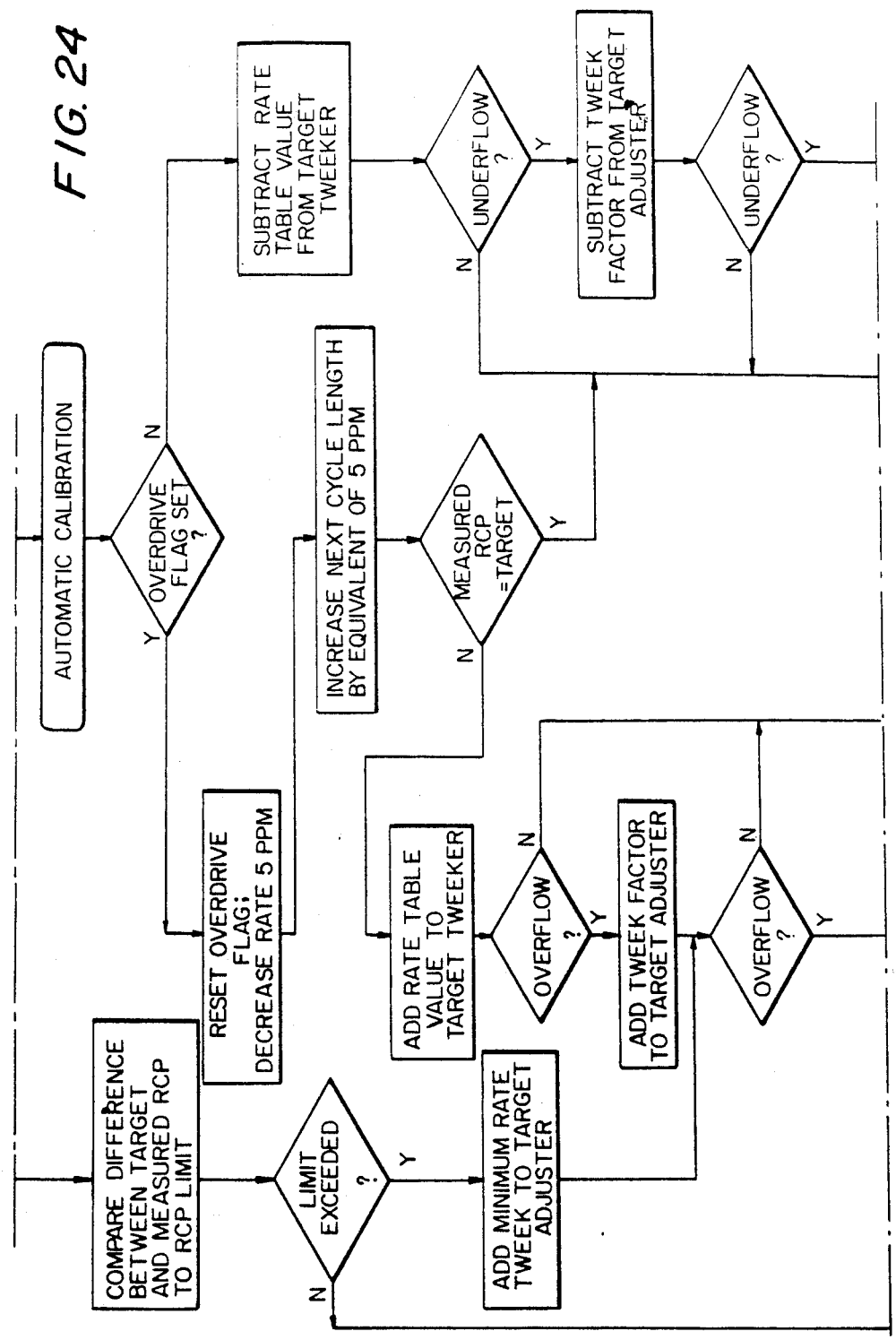
Figure 25:
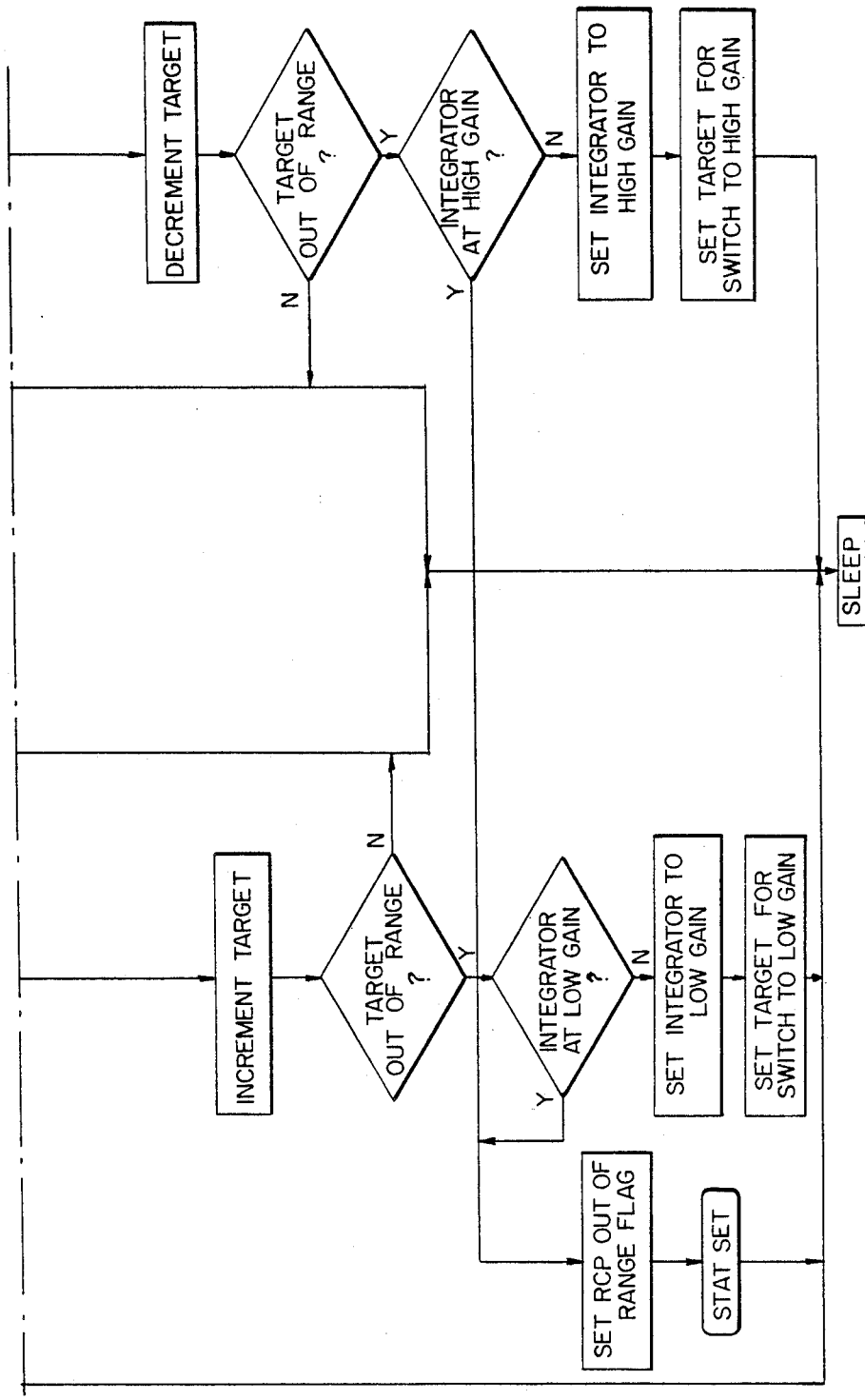

As shown on the flow chart of FIG. 24, after the minimum rate tweek is added to the target adjuster register, a check is made to see whether there has been an overflow from the adjuster register. If there has not been an overflow, the microprocessor is put to sleep, awaiting the end of the blanking period. If there has been an overflow, then as shown on FIG. 18 the value of target is incremented. As shown on FIG. 25, after target is incremented a check is made to see whether target has been incremented out of range. If not, the system waits for the end of blanking in the usual way. But if target has been incremented out of range, some additional processing is required.

The integrator which measures the RCP is provided with two possible gains. Target basically follows the RCP measurements, so that one way to decrease target so that it gets back within range is to decrease the gain of the integrator. Therefore, a test is made to see if the integrator is already set to have its low gain value. If it is, nothing can be done to get target back into range. The RCP out-of-range flag is set to indicate that rate response is no longer possible, and this information can be telemetered out to the programmer. Stat Set pacing (VVI, 70 ppm, 10 mA/1 ms) ensues, and the system awaits for the end of blanking in the usual way. On the other hand, if the integrator is not already set to have its low gain value, the gain value is now switched. Because this means that each RCP sample will be reduced in value, the present value of target also has to be reduced. At the bottom of FIG. 25 there is a step which provides for setting target for the switch to low gain, that is, reducing its value by the same factor by which the gain has been reduced—thereby bringing it back in range. Processing then continues in the usual fashion, with rate response still enabled.

Returning to the bottom of FIG. 23, the right branch is taken if the newly adjusted rate is somewhere between the minimum and maximum limits. Although the rate has been adjusted, it is still necessary to change target in accordance with either Rule 1 or Rule 3. The rate is above minimum rate, but it can be due to an intrinsic rhythm having made the pacer increase its rate in order to pace the heart so that an evoked potential could be measured (Case 3), or the rate may be above the minimum rate due to the rate response (Case 1). An overdrive flag, to be described below, is set when the pacing rate is increased, even though not called for by rate response, in order that a pacing pulse capture the heart so that an evoked potential may be processed. At the top of FIG. 24, the overdrive flag is examined. If it is set, representing Case 3, the overdrive flag is now reset, and the rate is decreased 5 ppm. The overdrive flag is reset so that another decrease in rate will not occur during a subsequent pass through the loop. The rate is decreased to compensate for the increase (to be described below) which ensured capture. (No matter how many times the rate may have been increased by 5 ppm in order that the pacing rate just exceed the intrinsic rate so that an evoked potential could be processed, only a single decrease of 5 ppm takes place; it is desirable to have the pacing rate just below the intrinsic rate.)

It will be recalled that when overdriving is necessary in order that a pacing pulse be generated so that an evoked response can be processed, separate and apart from decreasing the pacing rate by 5 ppm to cancel the overdrive, it is desirable to decrease the pacing rate by 5 ppm for only the next cycle; as described above, this helps ensure that the next intrinsic beat takes precedence over a paced beat. This is accomplished by the step of FIG. 24 which indicates that the next cycle length is increased by the equivalent of 5 ppm. (This terminology is used because it is not really the rate which is decreased since the decreased rate is applicable for only one cycle; it is perhaps more proper to talk in terms of increasing the cycle length.) The processing of target then continues. A test is performed to see if MRCP equals target. If it does, there is nothing further to do and a branch is taken to the bottom of FIG. 25 where the microprocessor is put to sleep awaiting the end of blanking. On the other hand, if the measured RCP is not equal to target, since what is being dealt with is Case 3, it is necessary to increase target, but at the slow rate of Case 1 rather than the fast rate of Case 2. Referring to FIG. 18, what is required in this case is the addition of a value from the rate table, which is dependent on the present rate, to the tweeker register. This step is shown in FIG. 24. A test is then made to see if there is an overflow from the tweeker register. If not, the microprocessor is put to sleep in the usual way. If there is an overflow, referring to FIG. 18 what is required is that the tweek factor be added to the adjuster register, and this is what the flow chart shows. Thereafter, the overflow test is performed to see whether target should be incremented, and the processing takes the path described above.

The only other case to consider is that in which the overdrive flag is not set, with a branch being taken to the right when the overdrive-flag-set test is performed; this branch is taken when the present rate is above the minimum rate due to rate response. Rule 1 requires that a value from the rate table be subtracted from the tweeker register, and this is shown in FIG. 24. A test is now performed to see if there is an underflow. If there is no underflow, the microprocessor is put to sleep and the system waits for an end to blanking. If there is an underflow, referring to FIG. 18 what is now required is that the tweek factor be subtracted from the adjuster register. This step is shown in the right path on FIG. 24. A test is then made to see if there is an underflow from the adjuster. If there is, target is decremented.

When target was incremented in Cases 2 and 3, a test was performed to see if target was out of range by reason of being too large. When target is decremented in Case 1, a comparable test is performed to see if it is out of range, but this time by reason of being too small. If it is not out of range, processing resumes in the usual manner with the system waiting for the end of blanking. But if target is too small, the system checks whether the integrator is set at its high gain. If it is, there is no way that the gain can be increased so as to increase target. The RCP-out-of-range flag is set and Stat Set pacing takes over. But if the integrator is presently at its low gain setting, the gain is switched to the high value. At the same time, because all values of RCP will be larger, the present value of target must be increased for the new high-gain operation (which is what brings target back into range). Processing then continues in the usual manner.

The microprocessor awakens with timeout of the blanking timer. (Referring to the top of FIG. 21, the timeout may occur at that point in the processing, as previously described. But in either case, an entry is made to the end blanking module on FIG. 26.) Blanking of the sense amplifier now ceases, and the rate timer is set. The rate timer times the escape interval, in accordance with the current rate if it has been adjusted by the rate response processing. If the blanking timer was set by the generation of a back-up pulse, then the escape interval is set not from the generation of the back-up pulse, but rather from 60 milliseconds earlier when the ordinary pacing stimulus was generated. The reason for this is that if the back-up pulse resulted from a fusion beat, the back-up pulse did not accomplish any function, and in order for the next pacing stimulus to capture the heart it should be timed from the fusion beat.

A test is then performed to see whether it is time for a threshold search. If it is not time, a branch is taken to the middle of FIG. 27 where the microprocessor is put to sleep again, this time waiting for a timeout of the rate timer. As described above, a threshold search is performed approximately once every twelve hours, or upon request by the programmer. If it is time for a threshold search, the first question is whether the search has already been instituted. (An example of a search-in-progress is represented by the setting of the search in progress flag on FIG. 22.) If a search is not yet in progress, three steps are executed. First, rate response is disabled because it is not operative during the search. Second, the signature flag is set because it is necessary to issue a two-pulse signature so that anyone reviewing an ECG trace will understand what is going on. Third, the output is set to 1 milliampere and the programmed starting pulse width, as described above in connection with the description of the threshold search routine depicted on FIG. 29. This is all that happens during the first pass through the steps on FIG. 26.

Figure 26:
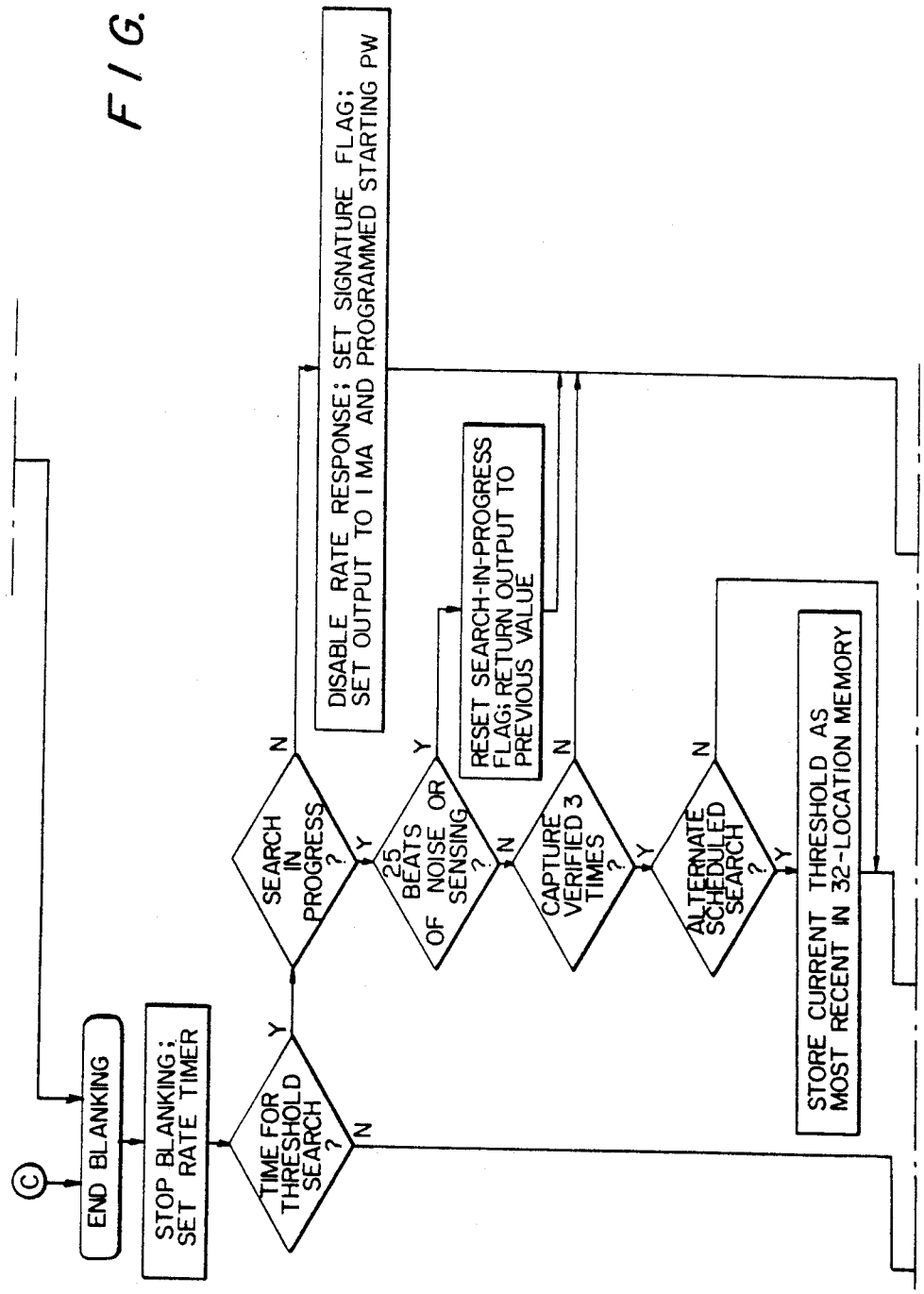

The next time around, or even the first time if the search-in-progress flag was set during the processing on FIG. 22, the search-in-progress question is answered affirmatively. If there have been 25 beats of noise or sensing since the threshold search began, the search is aborted, and the output is returned to its previous value. But if the search is on-going, the system checks whether capture has been verified three times. The actual incrementing of the output during a threshold search is performed on the left side of FIG. 22. The processing on FIGS. 26 and 27 is concerned more with what happened as a result of the completion of a threshold search or a regain of capture following a loss. In either event, the system checks whether capture has been verified three times in succession. As mentioned above, capture is verified three times to insure that a reliable threshold has been determined and to reduce the possibility of fusion beats causing a false indication of capture threshold. If capture has been verified three times, a test is performed to see whether the threshold search in progress is one of the "alternate scheduled." A threshold search is performed approximately every twelve hours. The system records the final threshold value on alternate searches so that it has available one threshold value for approximately each day. The 32 most recent threshold values are stored in a 32-location memory. It is of considerable aid to a physician to know on-going changes in the threshold during the first 30 days or so following implantation of a new lead. (The memory should have a minimum of 7 locations, for storing a week's worth of threshold values—at least one value per day.) The information is made available by telemetering it out of the pacemaker to a programmer.

Continuing with the flow chart on FIG. 27, following the determination of a new pulse energy value and its storage in memory, the search-in-progress flag is reset; the search is over. The output is also incremented two steps as a safety margin. The signature flag is set so that a pulse pair will serve to identify the completion of the threshold search. The system then determines the RCP sample time as described above, following which rate response is enabled once again if it has been programmed on. Thereafter, the pacemaker stops its processing and waits for the rate timer timeout.

If the rate timer times out, it means that a pacing pulse is required. The processing continues at point A on FIG. 19. On the other hand, if there is no rate timer time-out, it is because an intrinsic beat has been sensed. As shown at the bottom of FIG. 27, the system remains in a loop looking for either a timeout or an intrinsic beat. If it is an intrinsic beat which is the outcome, the "sensed" module on FIG. 2B is entered.

The first step in this module is to check whether what is believed to have been the sensing of an intrinsic beat fell within the refractory period. If it did, it is not treated as an intrinsic beat, and the loop at the bottom of FIG. 27 is re-entered so that the system can wait for either another sensing or a rate timer timeout. But if the sensed beat was outside the refractory interval, a test is made to see if the system is programmed to operate in the VVT mode. If it is, it means that every sensing is to be followed by a pacing pulse and the processing resumes at the top of FIG. 18. The processing on the right side of FIG. 28 is bypassed; this processing has to do with rate response, and rate response as well as automatic output regulation can be enabled only when the pacer is set to operate in the VVI mode.

Assuming that the pacer is operating in the VVI mode, the telemetry coil is pulsed for the same reason that it is on FIG. 20; the best time for programming to commence is immediately after the generation of a pacing pulse (FIG. 20) or immediately after the sensing of an intrinsic beat (FIG. 28), thereby lessening the chance of any interference with pacing functions by the programming. A sense marker is then outputted since an intrinsic beat has been sensed.

The processing on the right side of FIG. 28 pertains to overdriving (increasing the rate about the intrinsic rate) so that an evoked potential may be processed. The condition "overdrive enabled" means that rate response has been programmed on (in which case capture must be had so that an RCP measurement may be made), or—even if rate response has been programmed off—a periodic threshold search is being performed. (Even in the absence of rate response, in order to conserve energy the output amplitude and pulse width should not be unnecessarily high.) If overdrive is not enabled, it simply means that there is no reason to ensure that a paced event takes place so that an evoked potential can be measured, and processing continues at the top of FIG. 26 with entry into the end blanking module. Although the blanking timer has not been set and there is no blanking to stop, the processing does continue with setting of the rate timer; since an intrinsic beat has been sensed, the rate timer is set to time from this event.

If the overdrive enabled test is answered in the affirmative, it means that the rate should be increased to the point at which it just exceeds the intrinsic rate so that a paced event can take place in order for an evoked potential to be processed. However, this should happen only when it is appropriate. The first test which is now performed is to determine whether a threshold search is in progress (FIG. 29) or target initialization is in progress (FIG. 30). In either case, it is desired that there be a paced event in every cycle and a jump is taken to check whether the pacing rate is already at the maximum rate. If it is, there is no way in which it can be increased and a jump is made to the end blanking module on FIG. 26 where the rate timer is set. If neither a threshold search nor target initialization is in progress, a test is made whether the present cycle is the fourth since the last time that any evoked response measurement was made. If it is not, there is no reason to increase the pacing rate so that a paced event will occur instead of an intrinsic beat, and the end blanking module is entered. On the other hand, if it is the fourth beat and an evoked response is desired, since an intrinsic beat just took place overdrive is necessary. The maximum rate test is performed in this case as well as during a threshold search and target initialization.

If the present rate is not at the maximum, the rate is increased by 5 ppm and the overdrive flag is set. It will be recalled that it is the setting of the overdrive flag which controls the branching at the top of FIG. 24; the state of the flag is an indication whether the current rate, which is above the minimum, is due to overdriving or rate response. The rate is increased 5 ppm along with setting of the overdrive flag in order that the next stimulus capture the heart; the rate is decreased 5 ppm immediately following testing of the overdrive flag on FIG. 24 (which point is reached only if there has been a heart capture) when it is determined that the flag is set and that the rate was increased by at least 5 ppm in order to obtain a paced event. After setting the overdrive flag and increasing the rate on FIG. 28, the system moves on to the top of FIG. 26 to the end blanking module. It should be borne in mind that there may have to be several 5-ppm rate increases until capture is obtained, in which case the steps on FIG. 28 may be executed during each of several successive cycles. Nevertheless, there is only one 5-ppm rate reduction on FIG. 24 because the pacing rate should end up just below the intrinsic rate, unless, of course, it is increased by rate response.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. A pacemaker comprising means for generating pacing pulses; means for automatically adjusting the energy of said pacing pulses in order to ensure heart capture; means for sensing an evoked potential following the generation of a pacing pulse and responsive to the failure to sense an evoked potential for controlling operation of said adjusting means; means for determining that operation of said sensing means is unreliable due to the presence of noise; and means responsive to operation of said determining means for controlling said pacing pulses to be of predetermined energy.

2. A pacemaker in accordance with claim 1 wherein said sensing means senses an evoked potential by integrating the evoked potential and verifying that is exceeds a threshold value.

3. A pacemaker comprising means for generating pacing pulses; means for automatically adjusting the energy of said pacing pulses in order to ensure heart capture; and means for identifying operation of said adjusting means by providing a "signature" which consists of at least two closely spaced pacing pulses.

4. A pacemaker in accordance with claim 3 wherein said "signature" includes two closely spaced pacing pulses prior to an automatic adjustment and two closely spaced pacing pulses subsequent to the automatic adjustment.

5. A pacemaker comprising means for generating pacing pulses; means for controlling the pacemaker to automatically self-adapt to changing conditions; and means for identifying operation of said controlling means by providing a "signature" which consists of at least two closely spaced pacing pulses.

6. A pacemaker in accordance with claim 5 wherein said "signature" includes two closely spaced pacing pulses prior to an automatic adaptation and two closely spaced pacing pulses subsequent to the automatic adaptation.

7. A pacemaker comprising means for generating pacing pulses; means for automatically adjusting the energy of said pacing pulses in order to ensure heart capture; means for sensing an evoked potential following generation of a pacing pulse for determining if there has been a loss of heart capture; and means responsive to at least three successive operations of said determining means for initiating operation of said automatically adjusting means.

8. A pacemaker in accordance with claim 7 wherein said sensing means senses an evoked potential by integrating the evoked potential and verifying that is exceeds a threshold value.

9. A pacemaker comprising means for generating pacing pulses; means for automatically adjusting the energy of said pacing pulses in order to ensure heart capture; means for verifying at least three successive heart captures responsive to the generation of three successive pacing pulses following adjustment of the energy of said pacing pulses; and means responsive to operation of said verifying means for increasing the energy of said pacing pulses by a safety margin.

10. A pacemaker comprising means for generating pacing pulses; means for automatically adjusting the energy of said pacing pulses in the direction of increasing energy until heart capture is achieved; and means for programming operating parameters of the pacemaker, one of said operating parameters being the starting point for said automatic adjusting means.

11. A pacemaker in accordance with claim 10 wherein said one operating parameter is the width of a pacing pulse.

12. A method of operating a pacemaker comprising the steps of generating pacing pulses; automatically adjusting the energy of said pacing pulses in order to ensure heart capture; sensing an evoked potential following the generation of a pacing pulse and, responsive to the failure to sense an evoked potential, controlling execution of said adjusting step; determining that execution of said sensing step is unreliable due to the presence of noise; and, responsive to execution of said determining step, controlling said pacing pulses to be of predetermined energy.

13. A method of operating a pacemaker in accordance with claim 12 wherein an evoked potential is sensed by integrating the evoked potential and verifying that it exceeds a threshold value.

14. A method of operating a pacemaker comprising the steps of generating pacing pulses; automatically adjusting the energy of said pacing pulses in order to ensure heart capture; and identifying operation of said adjusting means by providing a "signature" which consists of at least two closely spaced pacing pulses.

15. A method of operating a pacemaker in accordance with claim 14 wherein said "signature" includes two closely spaced pacing pulses prior to an automatic adjustment and two closely spaced pacing pulses subsequent to the automatic adjustment.

16. A method of operating a pacemaker comprising the steps of generating pacing pulses; controlling the pacemaker to automatically self-adapt to changing conditions; and identifying execution of said controlling step by providing a "signature" which consists of at least two closely spaced pacing pulses.

17. A method of operating a pacemaker in accordance with claim 5 wherein said "signature" includes two closely spaced pacing pulses prior to an automatic adaptation and two closely spaced pacing pulses subsequent to the automatic adaptation.

18. A method of operating a pacemaker comprising the steps of generating pacing pulses; automatically adjusting the energy of said pacing pulses in order to ensure heart capture; sensing an evoked potential following generation of a pacing pulse for determining if there has been a loss of heart capture; and, responsive to at least three successive executions of said determining step, initiating execution of said automatically adjusting step.

19. A method of operating a pacemaker in accordance with claim 18 wherein an evoked potential by integrating the evoked potential and verifying that is exceeds a threshold value.

20. A method of operating a pacemaker comprising the steps of generating pacing pulses; automatically adjusting the energy of said pacing pulses in order to ensure heart capture; verifying at least three successive heart captures responsive to the generation of three successive pacing pulses following adjustment of the energy of said pacing pulses; and, responsive to execution of said verifying means for increasing the energy of said pacing pulses by a safety margin.

21. A method of operating a pacemaker comprising the steps of generating pacing pulses; automatically adjusting the energy of said pacing pulses in the direction of increasing energy until heart capture is achieved; and programming operating parameters of the pacemaker, one of said operating parameters being the starting point for said automatic adjusting step.

22. A method of operating a pacemaker in accordance with claim 21 wherein said one operating parameter is the width of a pacing pulse.

* * * * *